(12) United States Patent
Malik et al.

(10) Patent No.: US 8,883,088 B2
(45) Date of Patent: Nov. 11, 2014

(54) SAMPLE PREPARATION DEVICES AND SYSTEMS

(75) Inventors: Imran R. Malik, Pasadena, CA (US); Axel Scherer, Woodstock, VT (US)

(73) Assignee: California Institute of Technology, Pasadena, CA (US)

( * ) Notice: Subject to any disclaimer, the term of this patent is extended or adjusted under 35 U.S.C. 154(b) by 116 days.

(21) Appl. No.: 13/407,644

(22) Filed: Feb. 28, 2012

(65) Prior Publication Data

US 2013/0164754 A1 Jun. 27, 2013

Related U.S. Application Data

(60) Provisional application No. 61/580,035, filed on Dec. 23, 2011.

(51) Int. Cl.
*G01N 21/75* (2006.01)
*G01N 15/06* (2006.01)
*C12Q 1/68* (2006.01)
*C12P 19/34* (2006.01)

(52) U.S. Cl.
USPC ........... 422/417; 422/400; 422/68.1; 435/6.1; 435/6.12; 435/91.2

(58) Field of Classification Search
USPC ......... 422/400, 417, 68.1; 435/6.1, 6.12, 91.2
See application file for complete search history.

(56) References Cited

U.S. PATENT DOCUMENTS

| | | | |
|---|---|---|---|
| 4,930,361 A | 6/1990 | Nimberger | |
| 5,196,830 A | 3/1993 | Birging | |
| 5,272,518 A | 12/1993 | Vincent | |
| 5,508,197 A | 4/1996 | Hansen | |
| 5,820,265 A | 10/1998 | Kleinerman | |
| 5,871,699 A | 2/1999 | Ruggeri | |
| 6,222,619 B1 | 4/2001 | Herron et al. | |
| 6,441,890 B2 | 8/2002 | Wardlaw et al. | |
| 6,544,734 B1 * | 4/2003 | Briscoe et al. | 435/6.13 |
| 6,623,696 B1 | 9/2003 | Kim | |
| 6,902,112 B2 | 6/2005 | Sadler | |
| 7,411,792 B2 | 8/2008 | Richards et al. | |
| 7,564,541 B2 | 7/2009 | Tuschel | |
| 7,754,153 B2 | 7/2010 | Miyamoto | |
| 8,058,054 B2 | 11/2011 | Owen et al. | |
| 8,071,385 B2 | 12/2011 | Haas et al. | |
| 8,277,760 B2 * | 10/2012 | Lehto | 422/507 |
| 8,395,773 B2 | 3/2013 | Malik et al. | |
| 2002/0046614 A1 | 4/2002 | Alley | |
| 2002/0160534 A1 | 10/2002 | Herron et al. | |
| 2003/0109806 A1 | 6/2003 | Weber et al. | |
| 2004/0091862 A1 | 5/2004 | Brandenburg et al. | |
| 2004/0152206 A1 | 8/2004 | Davis et al. | |
| 2005/0024636 A1 | 2/2005 | Nakamura | |
| 2005/0036142 A1 | 2/2005 | Oldham et al. | |
| 2005/0042651 A1 | 2/2005 | Vann et al. | |
| 2005/0059165 A9 * | 3/2005 | Davis et al. | 436/514 |
| 2005/0099621 A1 | 5/2005 | Vez-Iravani et al. | |
| 2005/0109396 A1 | 5/2005 | Zucchelli et al. | |
| 2005/0282266 A1 | 12/2005 | Teng et al. | |
| 2006/0186346 A1 | 8/2006 | Wei | |
| 2006/0211071 A1 | 9/2006 | Andre et al. | |
| 2006/0289787 A1 | 12/2006 | Ohbian et al. | |
| 2006/0290934 A1 | 12/2006 | Boekelman | |
| 2007/0084279 A1 | 4/2007 | Huang et al. | |
| 2007/0272039 A1 | 11/2007 | Hermet et al. | |
| 2008/0003649 A1 | 1/2008 | Maltezos et al. | |
| 2008/0176230 A1 | 7/2008 | Owen et al. | |
| 2008/0176755 A1 | 7/2008 | Amundson et al. | |
| 2009/0050209 A1 | 2/2009 | Rautavuori et al. | |
| 2009/0176661 A1 | 7/2009 | Harding et al. | |
| 2010/0051124 A1 | 3/2010 | Imran | |
| 2010/0120164 A1 | 5/2010 | Salafsky | |
| 2010/0152066 A1 | 6/2010 | Malik et al. | |
| 2010/0192706 A1 | 8/2010 | Fairs et al. | |
| 2010/0321696 A1 | 12/2010 | Malik et al. | |
| 2011/0104026 A1 | 5/2011 | Yoon et al. | |
| 2011/0151577 A1 | 6/2011 | Zhang et al. | |
| 2011/0207137 A1 | 8/2011 | Malik et al. | |
| 2011/0207313 A1 | 8/2011 | Lim et al. | |
| 2011/0306120 A1 | 12/2011 | Nicholls et al. | |
| 2012/0003631 A1 | 1/2012 | Yu et al. | |
| 2012/0180882 A1 | 7/2012 | Malik et al. | |

FOREIGN PATENT DOCUMENTS

| | | |
|---|---|---|
| EP | 1972919 | 9/2008 |
| JP | 2002-139418 | 5/2002 |
| JP | 2002-214225 | 7/2002 |
| JP | 2012-100549 | 5/2012 |
| WO | 2000/21659 | 4/2000 |
| WO | 2007/102713 | 9/2007 |
| WO | 2011/005487 | 1/2011 |

OTHER PUBLICATIONS

PCT International Search Report mailed on Feb. 5, 2014 for PCT/US2013/068172 filed on Nov. 1, 2013 in the name of California Institute of Technology.

(Continued)

*Primary Examiner* — Ardin Marschel
(74) *Attorney, Agent, or Firm* — Steinfl & Bruno LLP

(57) ABSTRACT

Devices and system for preparing samples are described. Such devices can comprise fluidic chambers, reservoirs, and movable structures for controlling the movement of samples. The device can also comprise functional elements for performing specific operations.

19 Claims, 20 Drawing Sheets

(56) References Cited

OTHER PUBLICATIONS

PCT Written Opinion mailed on Feb. 5, 2014 for PCT/US2013/068172 filed on Nov. 1, 2013 in the name of California Institute of Technology.
Notice of Allowance mailed on Feb. 28, 2014 for U.S. Appl. No. 13/947,469, filed Jul. 22, 2013 in the name of California Institute of Technology.
PCT International Search Report mailed on Feb. 7, 2011 for PCT Application PCT/US2010/039389 filed on Jun. 21, 2010 in the name of California Institute of Technology et al.
PCT Written Opinion mailed on Feb. 7, 2011 for PCT Application PCT/US2010/039389 filed on Jun. 2010 in the name of California Institute of Technology et al.
PCT International Search Report mailed on Feb. 3, 2014 for PCT Application PCT/US2013/068170 filed on Nov. 1, 2013 in the name of California Institute of Technology.
PCT Written Opinion mailed on Feb. 3, 2014 for PCT Application PCT/US2013/068170 filed on Nov. 1, 2013 in the name of California Institute of Technology.
PCT International Search Report mailed on Feb. 17, 2014 for PCT Application PCT/US2013/068171 filed on Nov. 1, 2013 in the name of California Institute of Technology.
PCT Written Opinion mailed on Feb. 17, 2014 for PCT Application PCT/US2013/068171 filed on Nov. 1, 2013 in the name of California Institute of Technology.
PCT International Search Report mailed on Feb. 6, 2014 for PCT Application PCT/US2013/068173 filed on Nov. 1, 2013 in the name of California Institute of Technology.
PCT Written Opinion mailed on Feb. 6, 2014 for PCT Application PCT/US2013/068173 filed on Nov. 1, 2013 in the name of California Institute of Technology.
PCT International Search Report mailed on Oct. 16, 2013 for PCT Application PCT/US2013/051461 filed on Jul. 22, 2013 in the name of California Institute of Technology.
PCT Written Opinion mailed on Oct. 16, 2013 for PCT Application PCT/US2013/051461 filed on Jul. 22, 2013 in the name of California Institute of Technology.
PCT International Search Report mailed Feb. 17, 2014 for PCT Application PCT/US2013/068169 filed on Nov. 1, 2013 in the name of California Institute of Technology.
PCT Written Opinion mailed on Feb. 17, 2014 for PCT Application PCT/US2010/039389 filed on Jun. 21, 2010 in the name of California Institute of Technology et al.
PCT International Search Report mailed on Feb. 14, 2014 for PCT/US2013/068165 filed on Nov. 1, 2013 in the name of California Institute of Technology.
PCT Written Opinion mailed on Feb. 14, 2014 for PCT/US2013/068165 filed on Nov. 1, 2013 in the name of California Institute of Technology.
Final Office Action mailed on Jan. 24, 2014 for U.S. Appl. No. 12/638,829, filed Dec. 15, 2009 in the name of Imran R. Malik et al.
Final Office Action mailed on Oct. 23, 2013 for U.S. Appl. No. 12/638,829, filed Dec. 15, 2009 in the name of Imran R. Malik et al.
Non-Final Office Action mailed on Dec. 16, 2011 for U.S. Appl. No. 12/638,829, filed Dec. 15, 2009 in the name of Imran R. Malik et al.
Non-Final Office Action mailed on Oct. 3, 2013 for U.S. Appl. No. 12/638,829, filed Dec. 15, 2009 in the name of Imran R. Malik et al.
Restriction Requirement mailed on Oct. 20, 2011 for U.S. Appl. No. 12/638,829, filed Dec. 15, 2009 in the name of Imran R. Malik et al.
Final Office Action mailed on Oct. 10, 2012 for U.S. Appl. No. 12/820,104, filed Jun. 21, 2010 in the name of Imran R. Malik et al.
Non-Final Office Action mailed on Jun. 6, 2012 for U.S. Appl. No. 12/820,104, filed Jun. 21, 2010 in the name of Imran R. Malik et al.
Notice of Allowance mailed on Dec. 24, 2012 for U.S. Appl. No. 12/820,104, filed Jun. 21, 2010 in the name of Imran R. Malik et al.
Final Office Action mailed on Sep. 12, 2013 for U.S. Appl. No. 13/009,785, filed Jan. 19, 2011 in the name of Imran R. Malik et al.
Non-Final Office Action mailed on May 28, 2013 for U.S. Appl. No. 13/009,785, filed Jan. 19, 2011 in the name of Imran R. Malik et al.
Restriction Requirement mailed on Mar. 5, 2013 for U.S. Appl. No. 13/009,785, filed Jan. 19, 2011 in the name of Imran R. Malik et al.
Non-Final Office Action mailed on Nov. 26, 2013 for U.S. Appl. No. 13/407,644, filed Feb. 28, 2012 in the name of Imran R. Malik et al.
Restriction Requirement mailed on Sep. 17, 2013 for U.S. Appl. No. 13/407,644, filed Feb. 28, 2012 in the name of Imran R. Malik et al.

* cited by examiner

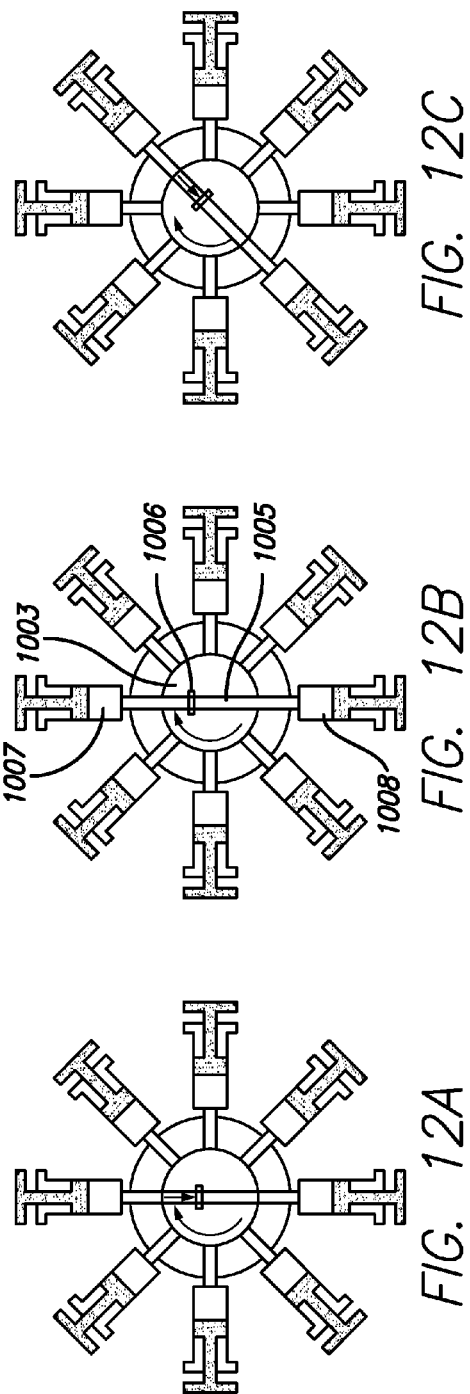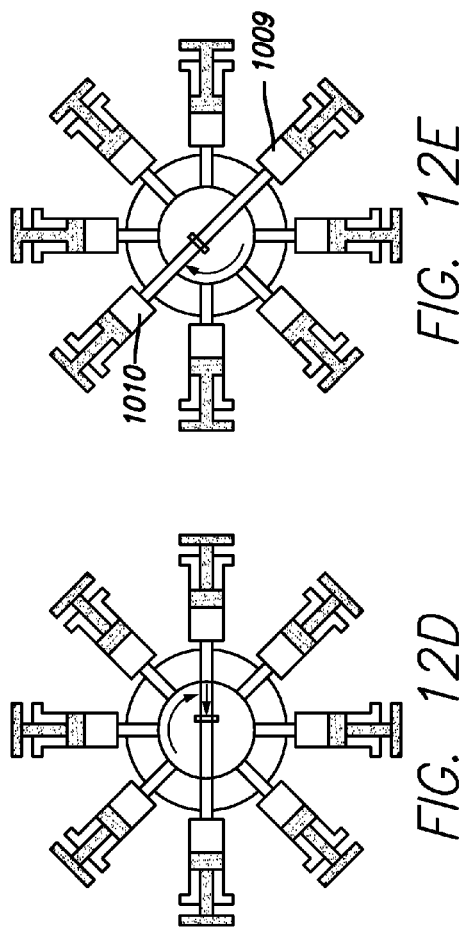

SAMPLE PREPARATION DEVICES AND SYSTEMS

CROSS REFERENCE TO RELATED APPLICATIONS

The present application claims priority to U.S. Provisional Application No. 61/580,035, filed on Dec. 23, 2011, which is incorporated herein by reference in its entirety.

FIELD

The present disclosure relates to fluidic devices that can facilitate preparation of samples. Moreover, it relates to sample preparation devices and systems.

BACKGROUND

A variety of methods are available to prepare fluidic samples for performing scientific experiments. However, some devices used for preparing samples can be expensive, bulky, and can have large dead volume space. Low cost, portable, reliable, and easy to use devices can be desirable to overcome such problems. With improved sample preparation devices, scientific analysis such as PCR, ELISA, or fluorescence/absorbance analysis can be perform more easily and accurately.

SUMMARY

According to a first aspect, a device for performing fluidic operations is described, the device comprising: a fluidic chamber having a plurality of pairs of ports, a first port of each pair being located on a first side of the fluidic chamber and a second port of each pair being located on a second side of the fluidic chamber, each second port being opposite a respective first port; a plurality of reservoirs adapted to be fluidly connected with the fluidic chamber at each of the plurality of pairs of ports, the plurality of reservoirs configured to flow fluid from a reservoir on the first side of the fluidic chamber to a reservoir on the second side of the fluidic chamber, or vice versa; and a structure slidably moveable within the fluidic chamber, the structure having one or more openings adapted to be aligned through sliding of the structure with at least one pair of ports to allow fluidic connection between one or more reservoirs on the first side and respective one or more reservoirs on the second side, the one or more openings being alignable with a desired pair of ports through said sliding.

According to a second aspect, a device for performing fluidic operations is described, the device comprising: an adapter comprising at least one pair of ports; a plurality of reservoirs fluidly connectable with the at least one pair of ports, the plurality of reservoirs configured to flow fluid from at least a first reservoir to at least a second reservoir; and a first structure associated with the adapter and displaceable with respect to the adapter, the first structure comprising a first channel arrangement configured to fluidly connect the at least first reservoir with the at least second reservoir, the first channel arrangement being alignable with a desired pair of ports through displacement of the first structure.

According to a third aspect, a device for performing fluidic operations is described, the device comprising: a first fixed structure and a second fixed structure having a plurality ports; a plurality of reservoirs adapted to be fluidly connected with the plurality of ports, the plurality of reservoirs configured to flow fluid from a reservoir associated with the port on the first fixed structure to a reservoir associated with the port on the second fixed structure, or vice versa; and a structure slidably moveable between the first fixed structure and the second fixed structure, the structure having one or more openings adapted to be aligned through sliding of the structure with at least one port of the first fixed structure and at least one port of the second fixed structure to allow fluidic connection between one or more reservoirs associated with the first fixed structure and respective one or more reservoirs associated with the second fixed structure, the one or more openings being alignable with a desired pair of ports through said sliding.

According to a fourth aspect, a method of performing fluidic operations using the device according to claim 2 is described, the method comprising: a) slidably moving the structure to align the at least one opening with a first pair of ports; b) transferring the fluid from the reservoir on the first side of the fluidic chamber to the reservoir on the second side of the fluidic chamber by flowing the fluid through the functional element in the opening; and c) repeating a)-b) a desired number of times.

BRIEF DESCRIPTION OF DRAWINGS

The accompanying drawings, which are incorporated into and constitute a part of this specification, illustrate one or more embodiments of the present disclosure and, together with the description of example embodiments, serve to explain the principles and implementations of the disclosure.

FIGS. 10, 11, and 12A-12E show cross-sectional and perspective views of fluidic devices with a displaceable structure.

DETAILED DESCRIPTION

Some embodiments of the present disclosure describe devices, systems and methods for performing fluidic operations and fluidic routing. Samples can be prepared for various diagnostic and analytical tests, fluid routing, complex manifold replacement as well as other operations. Some embodiments can allow for manual and/or automated operation. The invention allows rapid and reliable operation. It is low cost and obviates many problems possessed by present design and systems.

In some embodiments, complex fluid routing and operations can be performed without (or with fewer number of) valves and channels. Furthermore, dead volume space can be very low (or zero) for fluid movement between fluids located at relatively long distances. The invention allows a universal way to perform very complex fluidic operations with a much simpler design. A sequence of operation can be established on-the-fly depending on type of sample thus allowing universal sample processing units. It also allows mix and match and on the fly reconfiguration and design, thus being a truly modular and customizable. It allows flexibility in sequence of operations depending on sample type. It allows parallel operations in some cases allowing multiple operations to run at the same time. The invention is useful for cartridge, lab on chip and other design approaches. The invention allows scalable design and the devices on these concepts can be made of a large range of dimensions. It also allows universal sample type input capability. Although we describe sample preparation for examples, the invention is also useful for wide variety of applications including fluid manipulation, chemical and biological analysis, food safety, drug testing, fluid metering and many others.

Figure 1:
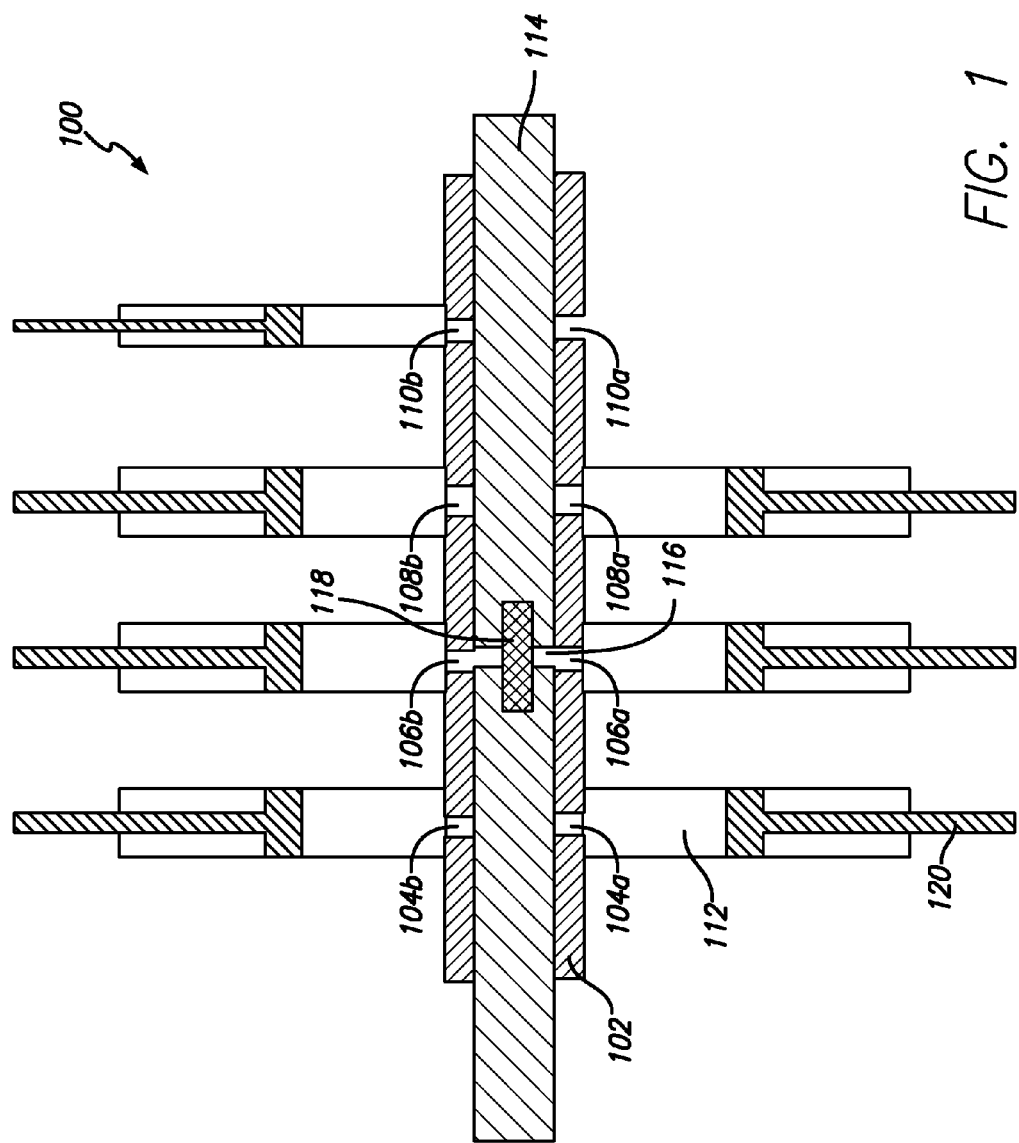
FIGS. 1-7 show cross-sectional views of exemplary fluidic devices with a structure being slidably moveable in an axial direction.

FIG. 1 shows an exemplary device 100 for performing fluidic operations. In some embodiments, the device 100 can comprise a fluidic chamber 102 having a plurality of ports 104a/b-110a/b. The ports can be configured in pairs such that a respective port for a particular port is located on an opposite side of the fluidic chamber 102, as shown, for example, port 104a and a respective port 104b, and so on.

In some embodiments, a plurality of reservoirs can be fluidly connected (e.g., luer connection) with the fluidic chamber 102 at one or more of the ports. Such configuration allows for flowing fluid from the reservoir to or through the fluidic chamber 100 to another reservoir connected with an opposite side of the fluidic chamber 102 at another port. By way of example and not of limitation, reservoirs can be syringes, custom shaped syringes, tubes with or without pinching mechanisms, planar reservoirs and channels with a chip, pouches, collapsible pouches, reagent storage, or cartridges. However, those skilled in the art would understand that other types of reservoirs can also be utilized.

In some embodiments, a slidably moveable structure 114 can be located within the fluidic chamber 102. Such moveable structure 114 can have an opening 116 such that when the opening 116 is aligned with one or more ports (e.g., ports 106a and 106b), fluid is able to flow from one reservoir to another reservoir, through the opening.

In some embodiments, the opening 116 in the moveable structure 114 can comprise a functional element 118. A functional element 118 can be defined as a something that performs a particular function when the fluid flows through the opening 116. By way of example and not of limitation, functional elements 118 can be one or more of a DNA binding matrix, lysis structure, plasma filter, cell filter, mixing filter, binding filter, washing element, mixing element, bacteria filter, virus filter, cytometry, analysis element, de-bubbler, di-electrophoresis, impedance spectroscopy, fluorescence/absorbance measuring elements, clear channel, capillary filling, and/or droplet generation. Therefore, when the fluid flows through the opening 116, the fluid can have an interaction with the functional element 118. In the case of the DNA binding matrix, when a fluid containing DNA flows through the DNA binding matrix, the DNA binds to the matrix, thus capturing the DNA.

In some embodiments, a fluidic pressuring mechanism 120 can be configured to facilitate movement of the fluid from the associated reservoir to the fluidic chamber 102. Such fluidic pressuring mechanism 120 can be, by way of example and not of limitation, pistons, actuators, pumps, or valves. Pistons can have various sizes and shapes, for example, to function with a syringe. Actuators can be internal to the reservoir or external to the reservoir. Pumps can also be internal or external to the reservoir, and can be electrochemical pumps, parasitic pumps, electro-osmotic pumps or vacuum pumps. Electro-osmotic pumps can be used to pump elute buffer with DNA in the cartridge. In some embodiments, a membrane can be used to press down in the reservoir, thus forcing the fluid to flow. The fluidic pressure obtained from such fluidic pressuring mechanism can comprise positive or negative pressure. For example, the fluid can be pushed from the source of the fluid, or pulled from the destination of the fluid. However, those skilled in the art would understand that other types of pressuring mechanisms are possible to facilitate the movement of the fluid.

Figure 2A:
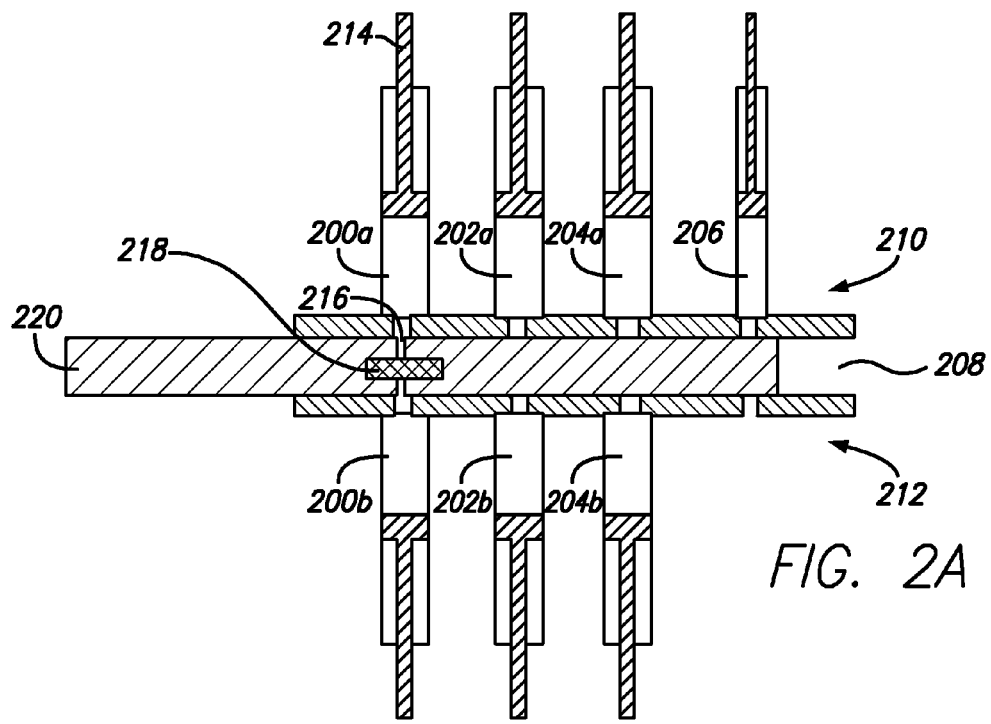
Figure 2B:
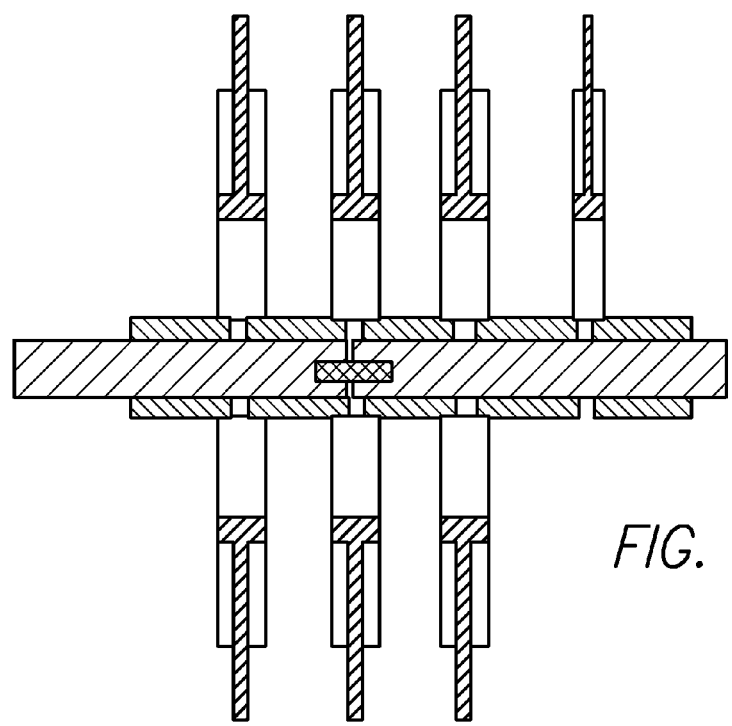
Figure 2C:
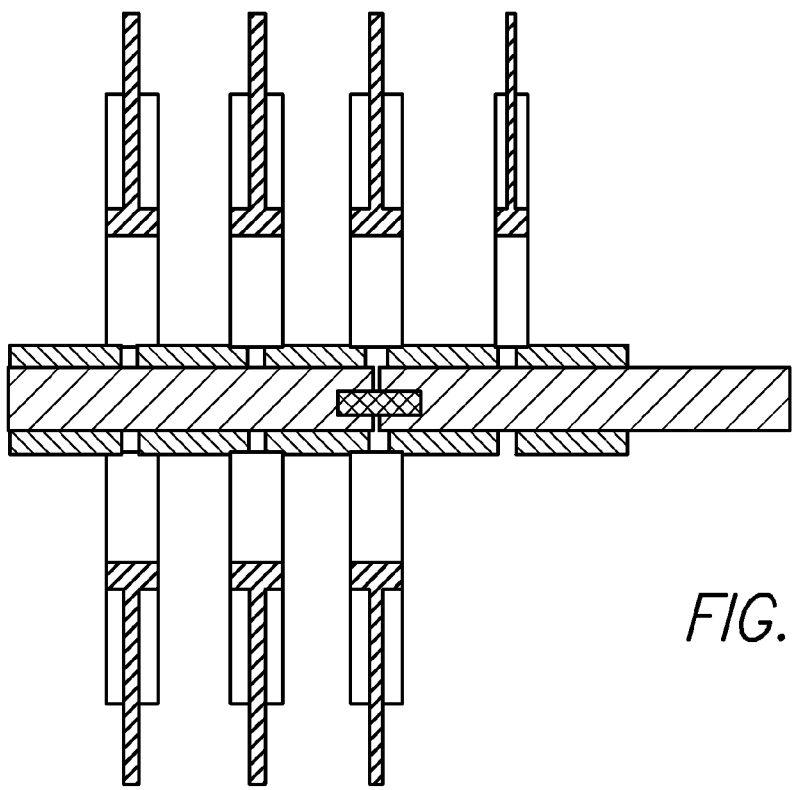
Figure 2D:
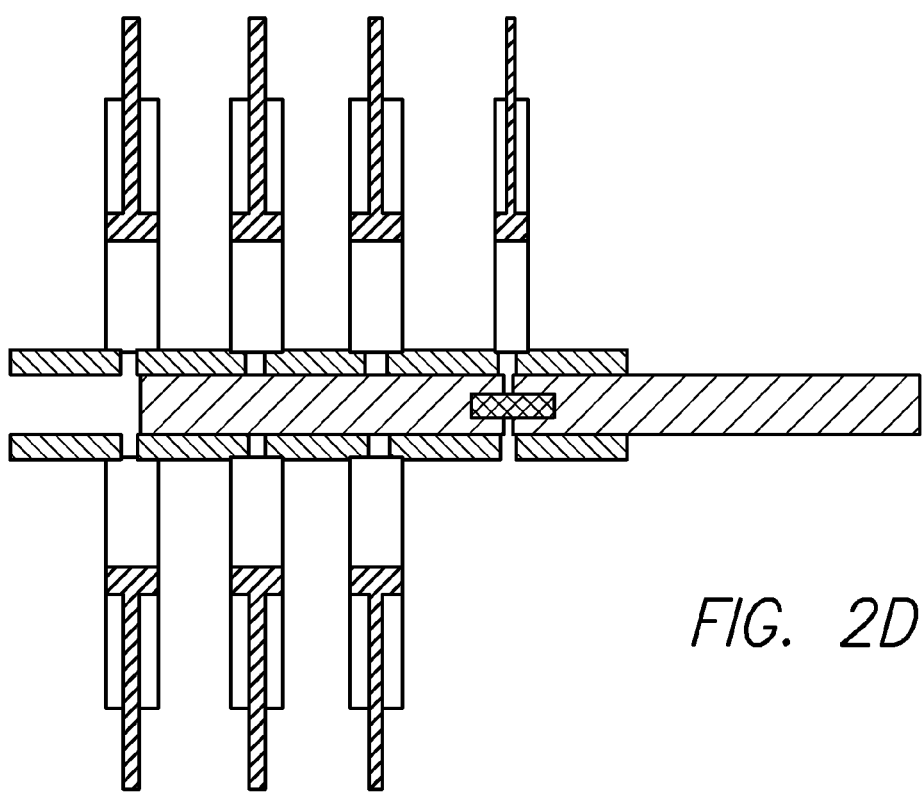

FIGS. 2A-2D shows an exemplary fluidic procedure for obtaining DNA. By way of example and not of limitation, a first reservoir 200a on a first side 210 of the fluidic chamber 208 can contain a fluidic sample such as a lysate mixture. The fluidic pressuring mechanism 214 can push the lysate mixture from the first reservoir 200a on the first side 210 of the fluidic chamber 208 to a first reservoir 200b on a second side 212 of the fluidic chamber 208, through the opening 216 in the moveable structure 220. As the fluid flow through the opening 216, the functional element 218 (e.g., DNA binding matrix) can capture the DNA and the fluid can continue to flow through/past the functional element 218, to the second reservoir 200b. Once the DNA is captured in the functional element 218, the moveable structure 220 can be moved to a second position as shown in FIG. 2B. In the configuration shown in FIG. 2B, the moveable structure 220 is slid to the right such that the opening 216 is now aligned with a pair of second reservoirs 202a/b. The second reservoir 202b on the first side 210 of the fluidic chamber 208 can comprise a solution, by way of example and not of limitation, water to wash the DNA that is captured in the functional element 218 (e.g., DNA binding matrix). The fluidic pressuring mechanism 214 can be used again to push the water from the second reservoir 202a on the first side 210 of the fluidic chamber 208 to the second reservoir 202b on the second side 212 of the fluidic chamber 208. A process can be repeated as many times as desired as shown in FIG. 2C according to the fluidic operation being performed, which can be determined by those having ordinary skill in the art. Finally, in the exemplary embodiment shown in FIG. 2D, a fourth reservoir 206 can comprise an elution buffer to elute the DNA from the functional element 218 (e.g., DNA binding matrix). A cartridge or a pouch can be connected with the second side 212 of the fluidic chamber 208 to collect the DNA as a result of the elution. An external ultrasonic or vibration device can be coupled with the reservoir (internally or externally) to mix the fluid in the reservoir.

Figure 3:
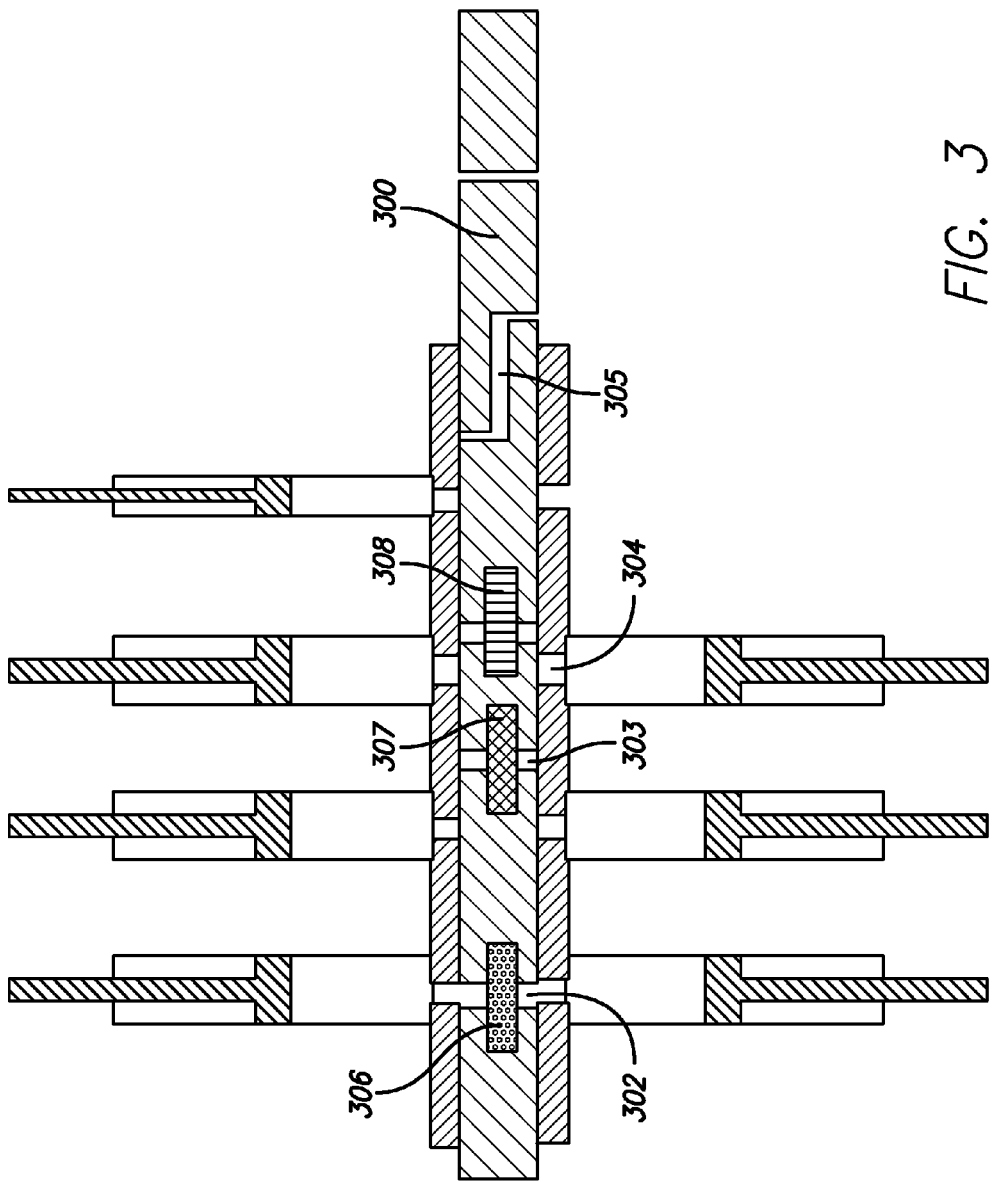

In some embodiments, the moveable structure 300 shown in FIG. 3 can comprise more than one openings 302-305. Each of the openings can comprise the same or different functional elements 306-308 according to the desired fluidic operation to be performed. In some embodiments, the opening 305 does not necessarily comprise a functional element. Alternatively, the opening 305 can comprise a channel for routing the fluid from one reservoir to another reservoir. In some embodiments, the fluidic chamber can comprise more than one moveable structures, one on top of another. Such moveable structures can slides in an axial direction as shown or along a curved path. Therefore, more than one application or operation can be performed simultaneously. The temperature of the fluidic device can be controlled to optimize functionality (e.g. bonding condition) of the functional element.

Figure 4A:
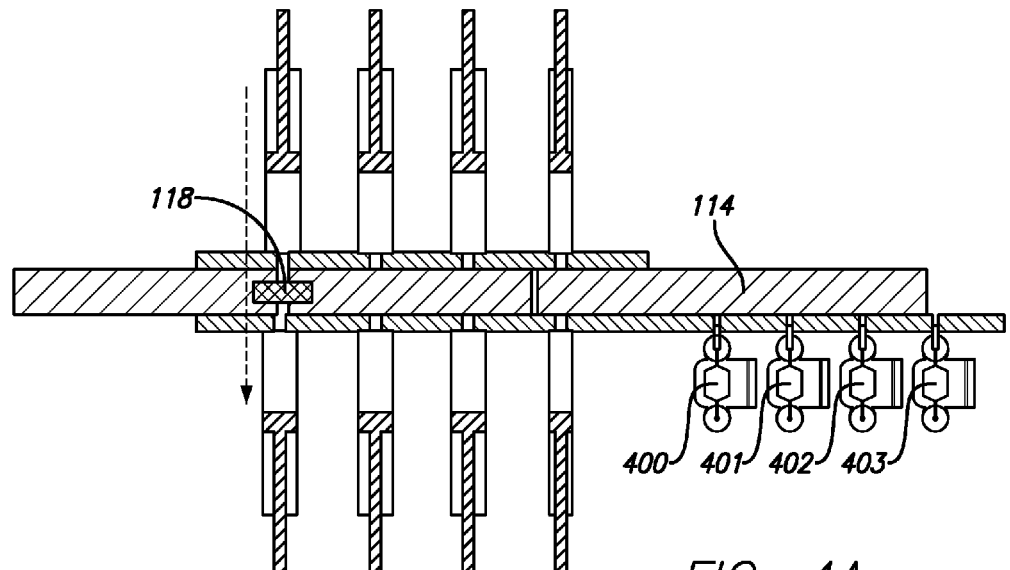
Figure 4B:
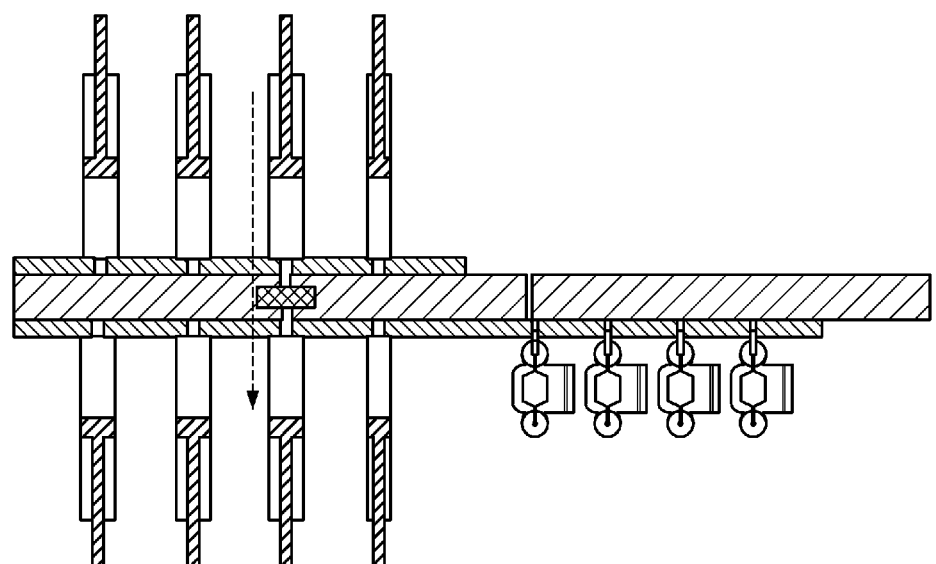
Figure 4C:
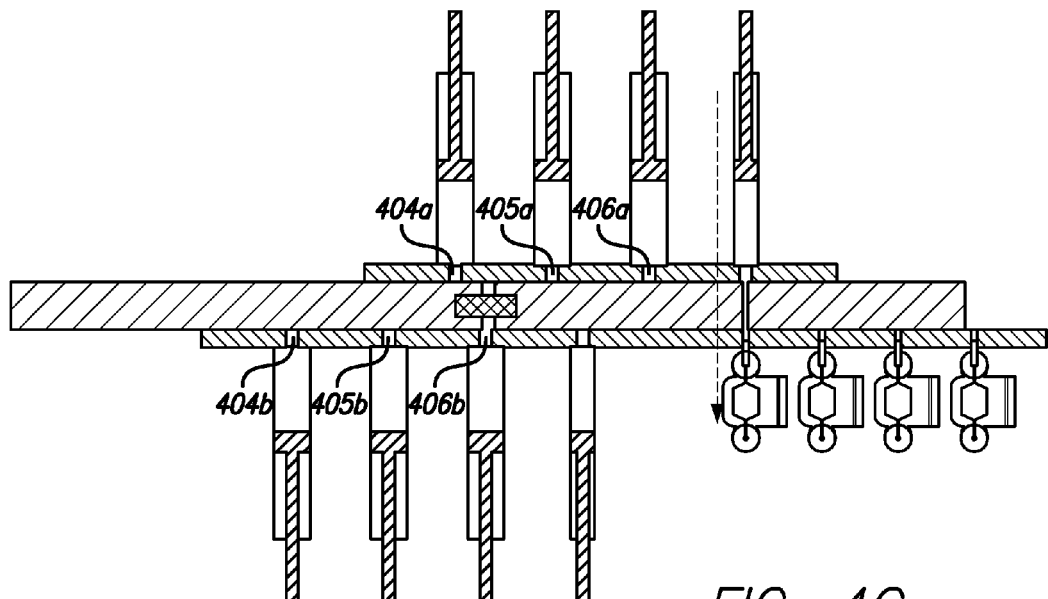
Figure 4D:
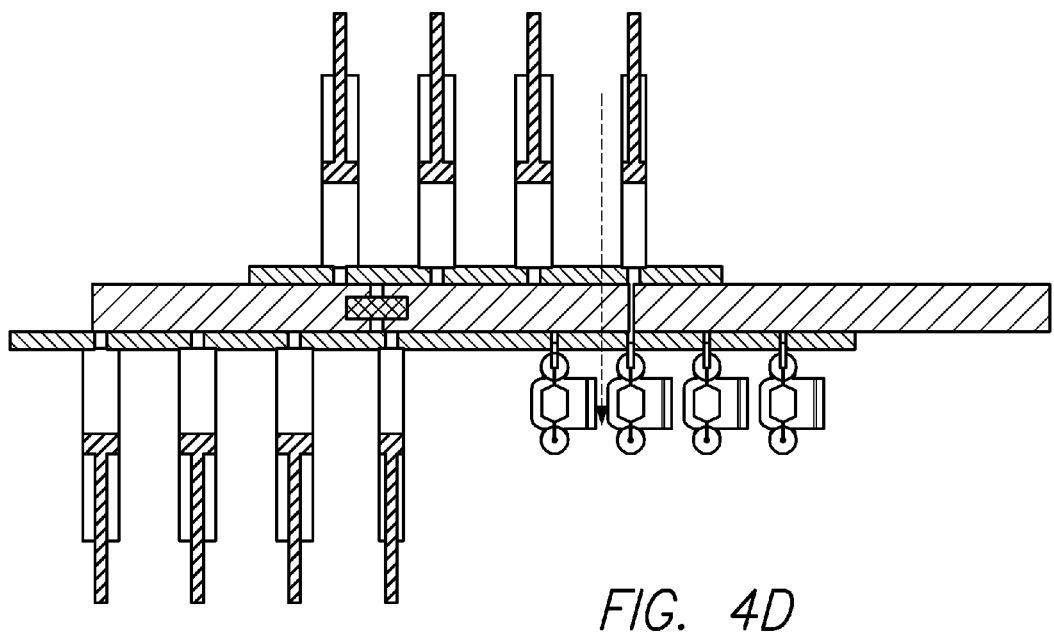

FIGS. 4A-4D show alternative configurations of the fluidic chamber and reservoirs. By way of example and not of limitation, FIG. 4A shows cartridges 400-403 as reservoirs in addition to those shown in FIGS. 1-3. Accordingly, the moveable structure 114 can be moved along an axial direction of the device to perform the fluidic operation and ultimately fill the cartridges 400-403 with, for example, DNA from the functional element 118. Additionally, as shown in FIGS. 4C-4D, the pair or ports 404a/b-406a/b are not necessarily located directly opposite to its respective port. Alternatively, the cartridges can be replaced with tubes or well plate. Examples of applications using the method shows in FIGS. 4A-4D can include, for example, but not be limited to separating serum and plasma for ELISA or other immunoassay operations. Results can be read using, for example, fluorescence or other methods known by those skilled in the art.

Figure 5:
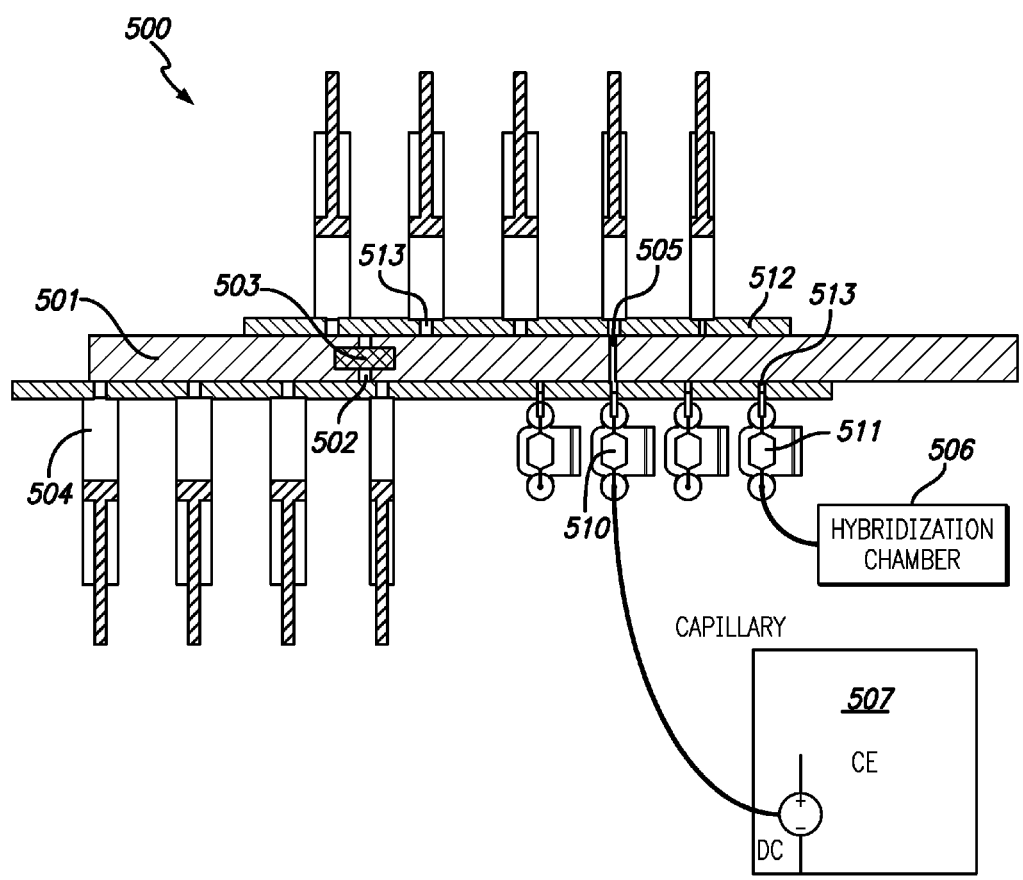

FIG. 5 shows an exemplary configuration of the fluidic device 500 when used to perform, for example, sample preparation for Polymerase Chain Reaction (PCR). The fluidic chamber 512 can comprise a plurality of ports 513 and have a moveable structure 501 configured to slide within the fluidic chamber 512. The moveable structure 501 can have a first opening 502 with a functional element (e.g., DNA binding matrix) and a second opening 505 without a functional element. The plurality of reservoirs 504 (e.g., syringes) and the moveable structure 501 can be used to wash and elute the sample in a sequence as described in previous paragraphs. Cartridges 510, 511 can also be connected with the ports 513 and the cartridges can be further connected with other devices such as a hybridization chamber 506 or capillary electrophoresis 507. The syringes used can be low cost syringes and the syringe can be direction applied to the fluidic chamber 512. As a consequence of the moveable structure 501, the fluidic chamber 512 can be valveless and channels having dead volume can be minimized in the fluidic chamber 512. The amount of dead volume space is unaffected by varying the size and/or relative distances of the reservoir 504 and the moveable structure 501 since when the moveable structure 501 is aligned with the ports 513, the entire opening 502 is part of the flow path of the fluid. When the moveable structure 501 is moved to a new position, the same opening can be used at the flow path, thereby almost completely eliminating any dead volume space.

In some embodiments, the syringes and the moveable structure 501 can be operated manually by a user or the entire operation can be automated by, for example, motors configured to move the moveable structure 501, operate the syringes, and/or the hybridization chamber 506. In some embodiments, a motor with a screw can be used to drive the moveable structure. For rotary design moveable structures, a stepper motor can be used. A single fluidic device can comprise both manual and automated operation so that in cases where power is unavailable (e.g., dead battery, emergency), manual operation can be used. The entire fluidic device can be a closed system thus avoiding contamination issues.

In some embodiments, multiple lysis operations can be integrated in the reservoir and the moveable structure. For example, tough bacteria or gram positive bacteria can have beads. In such case, the sample can be placed in a lysis reservoir. Alternatively, there can be beads inside the moveable structure or the reservoir for bead beating. In some embodiments, cells greater than certain sizes can be retained to perform lysis, which can be helpful in the case of Malaria. In some embodiments, different DNA and/or RNA can be obtained through different sequences from the same sample from a person. Some embodiments allows for on-the-fly or field mix-and-match of modules for sample processing.

Figure 6:
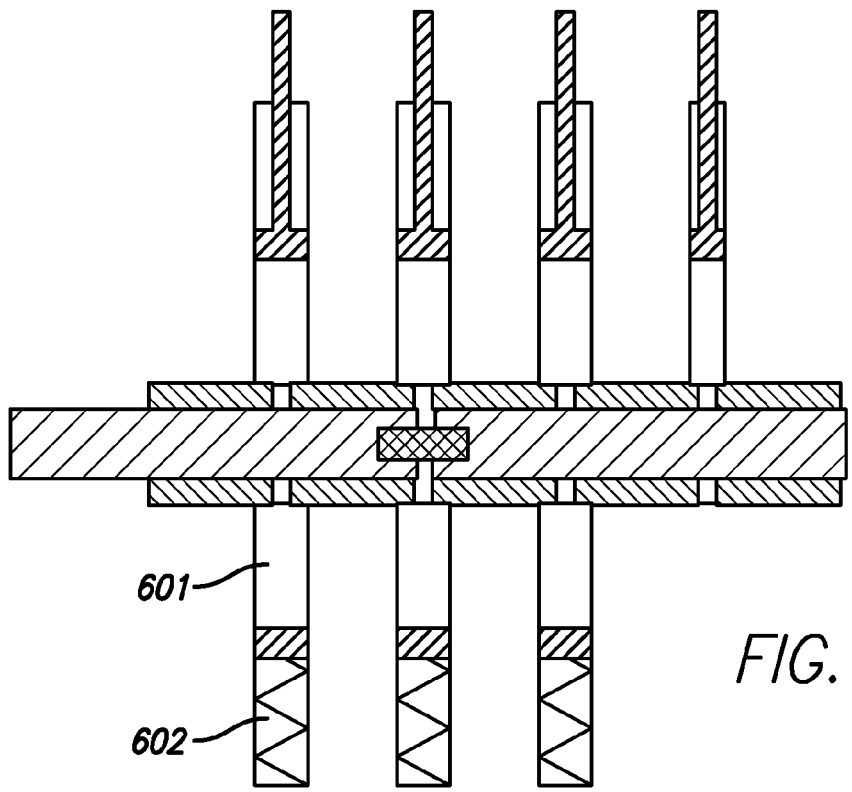
Figure 7:
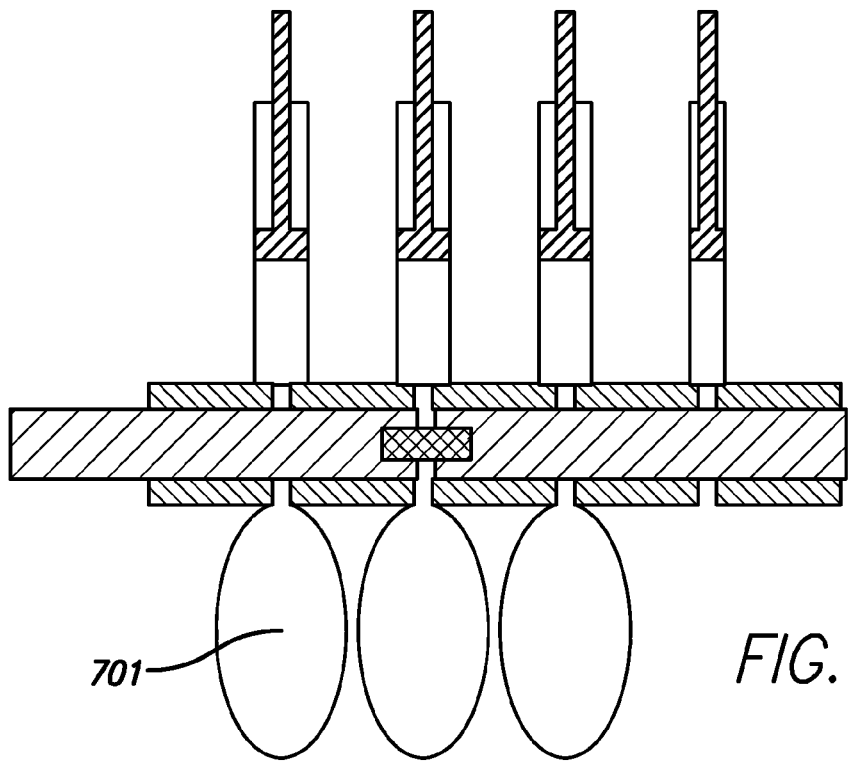

FIGS. 6-7 show alternative configurations of the fluidic device. For example, the reservoirs 601 in FIG. 6 is shown with springs 602 to cause movement of the fluid from the reservoir. FIG. 7 is shown with a flexible pouch 701 as reservoirs.

Figure 8:
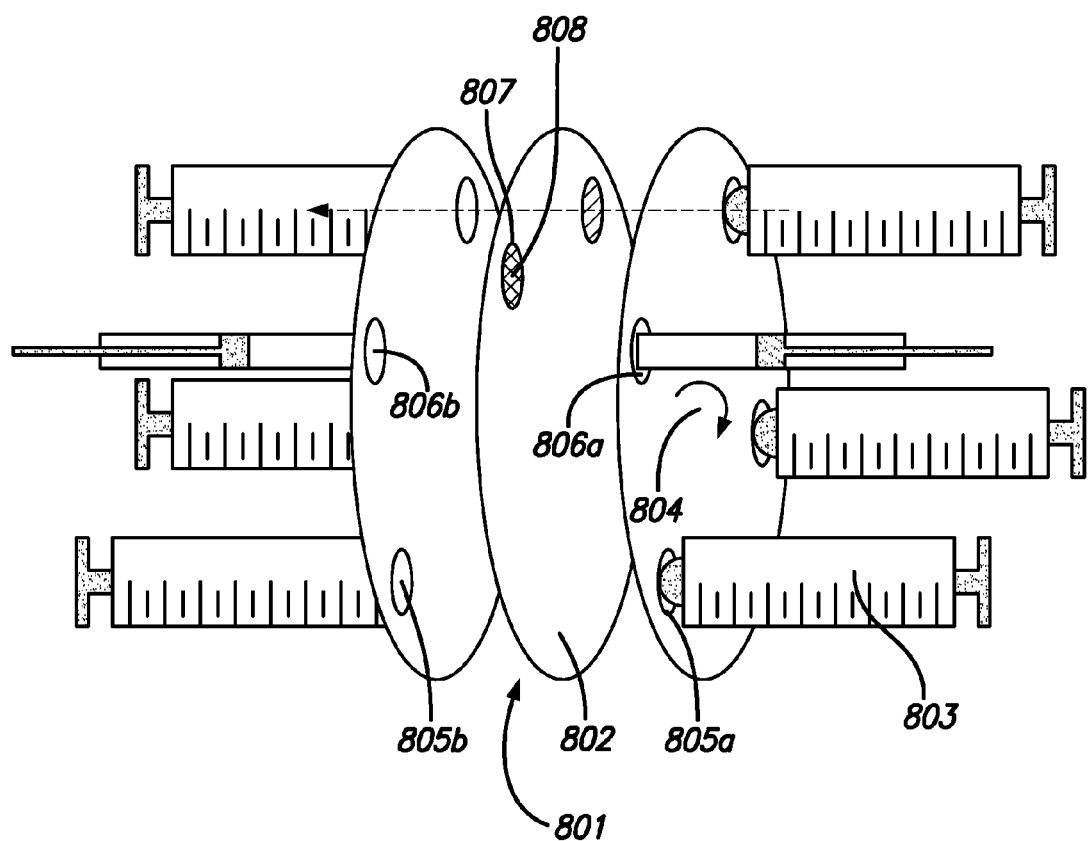
FIGS. 8-9 show cross-sectional views of exemplary fluidic devices with a structure being slidably moveable in a radial direction.
Figure 9A:
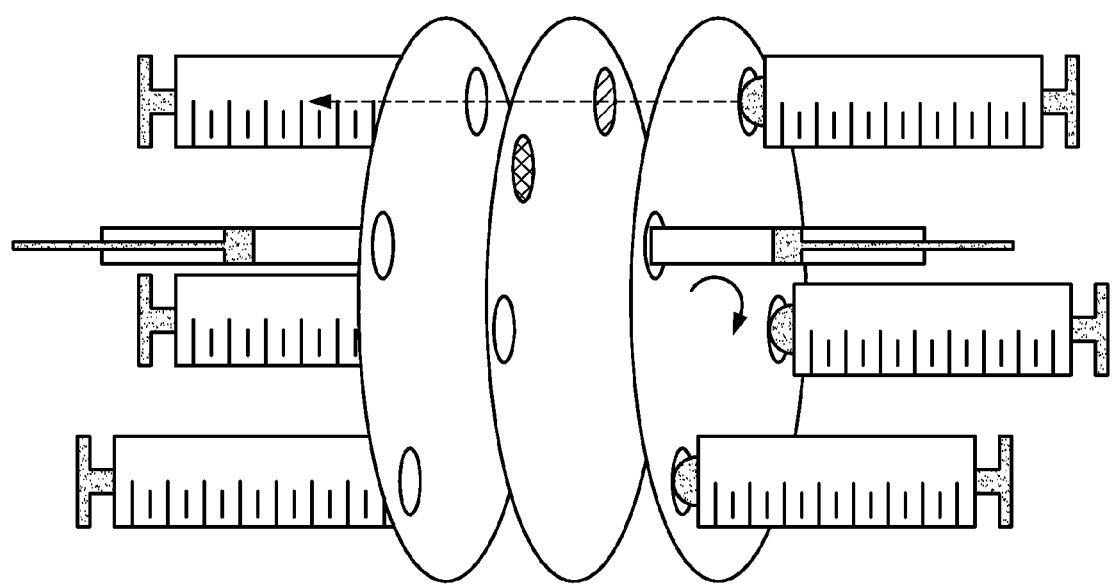
Figure 9B:
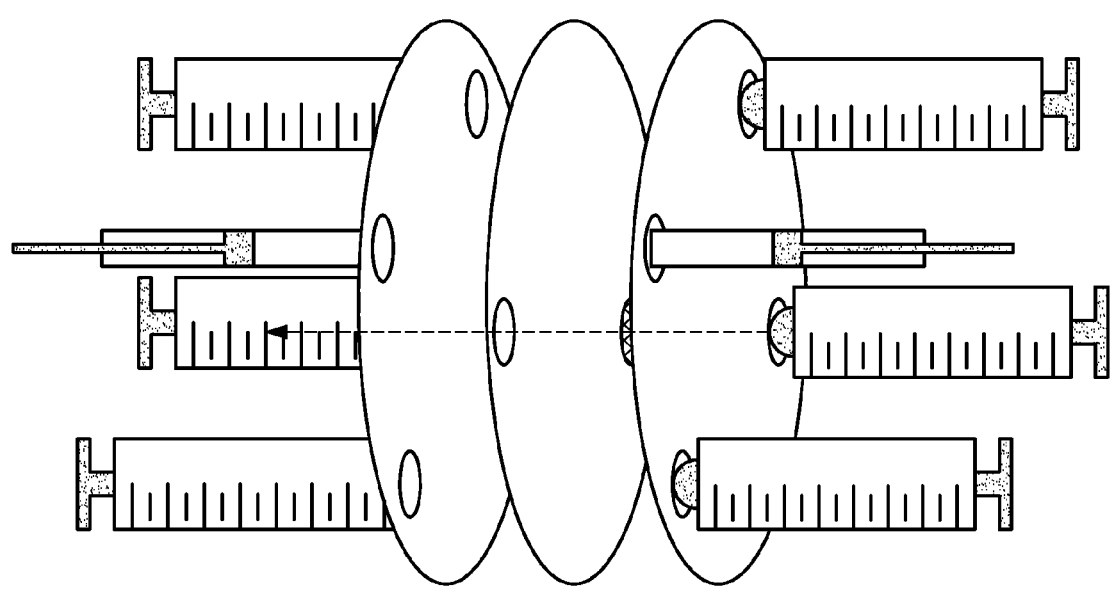
Figure 9C:
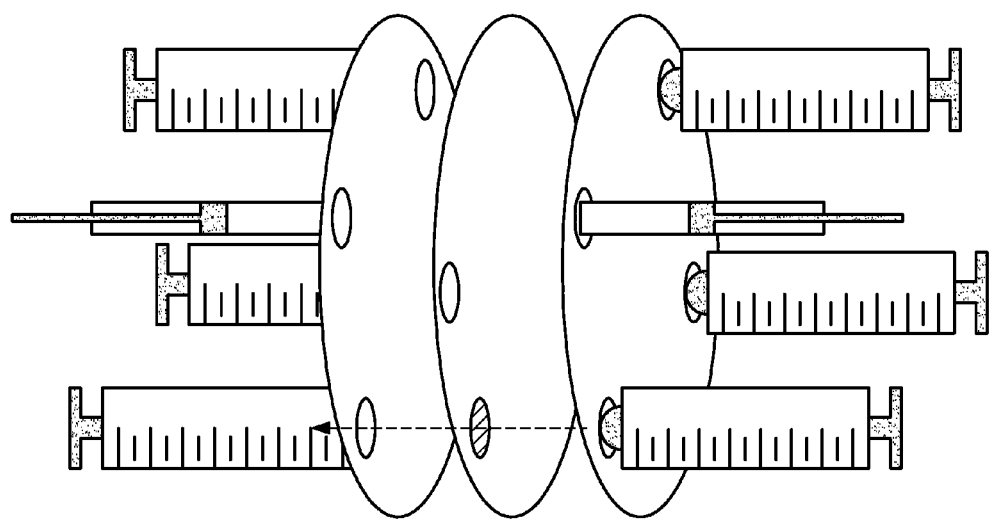
Figure 9D:
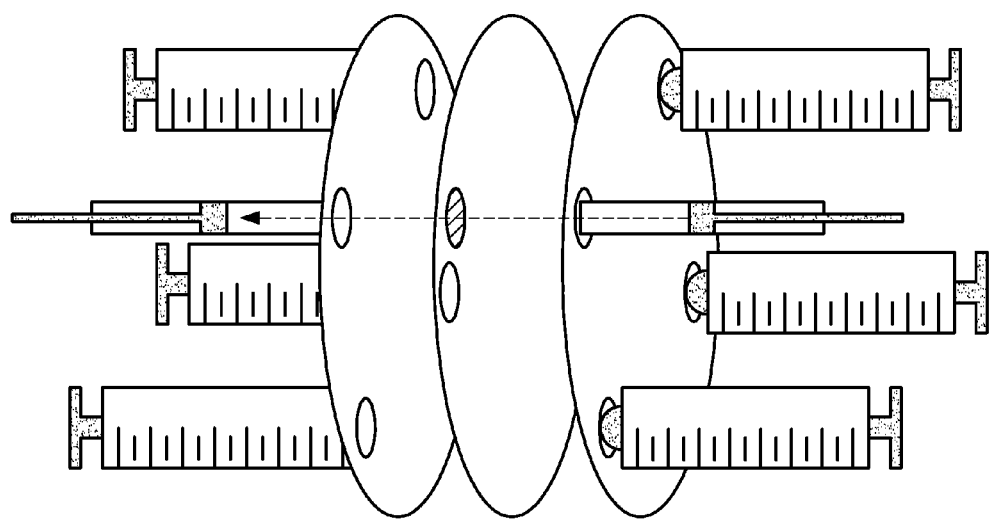

FIG. 8 shows an exemplary embodiment of a fluidic device 800 having a moveable structure 802 that can be configured to slide in a radial direction of the device as shown with arrow 804. Similarly to the configuration of the fluidic devices shown in FIGS. 1-7, the fluidic device 800 in FIG. 8 has a plurality of ports 805a/b-806a/b and reservoirs 803. The moveable structure 802 can comprise one or more openings 807, which can be aligned with the plurality of ports such that when the opening is aligned, by way of rotating the moveable structure 802, the fluid can flow from the reservoir on a first side of the reservoir to a second side of the reservoir. Accordingly, the opening 807 can comprise a functional element 808 such as a DNA binding matrix.

FIGS. 9A-9D show a fluidic process that can be equivalent to the exemplary fluidic procedure for obtaining DNA as shown in FIGS. 2A-2D using a moveable structure 802 that can rotate radially.

Figure 10:
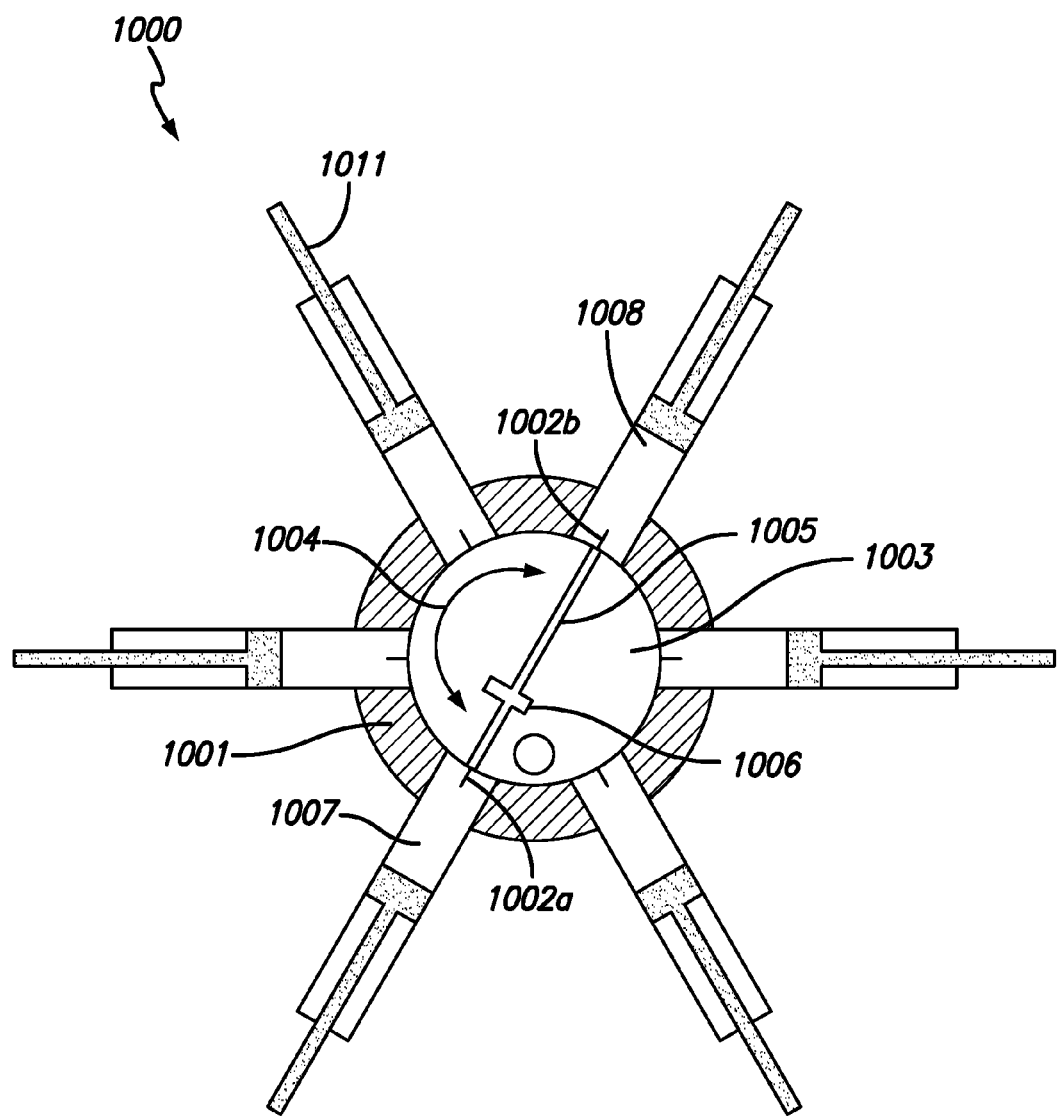
Figure 11:
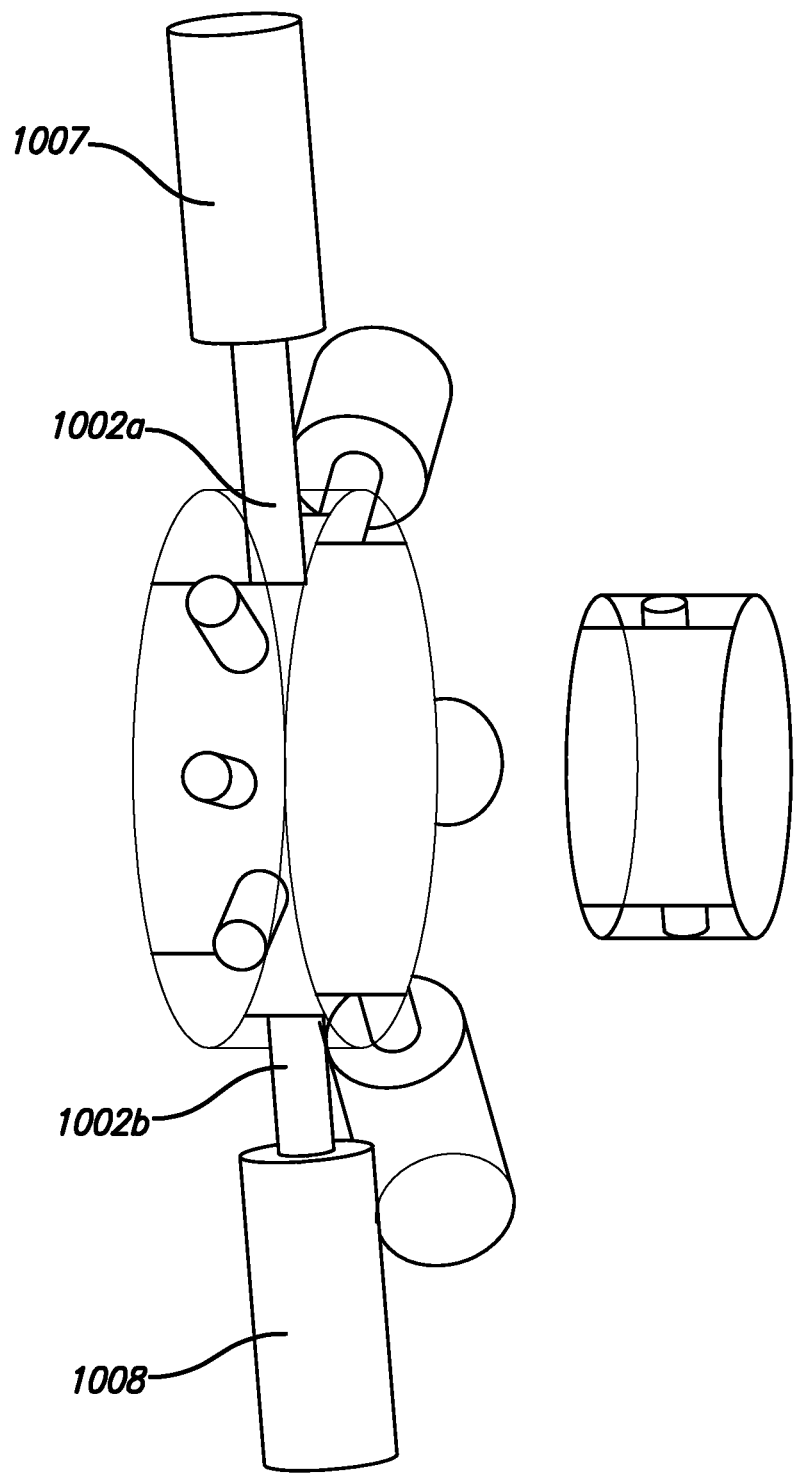

FIGS. 10-11 show another exemplary fluidic device 1000 for performing fluidic operations, similarly to the device described for FIGS. 1-9. The device 1000 can comprise an adapter 1001 having at least one pair of ports 1002a/b, and a plurality of reservoirs 1007, 1008 that can be connectable with the ports. The device 1000 can also comprise a structure 1003 that can be displaceable with respect to the adapter 1001. By way of example and not of limitation, the structure 1003 can rotate in radial direction as shown with an arrow 1004. The structure can comprise a fluidic channel arrangement 1005 adapted to allow fluid to flow. The channel arrangement 1005 can be a single channel or a plurality of channels making up the channel arrangement 1005. The channel arrangement 1005 can comprise a functional element 1006 within the fluidic path of the channel arrangement 1005.

In some embodiments, the plurality of channels can be adapted to allow flow cytometry using fluorescence, absorbance, impedance or other detection mechanism. Hydrodynamic focusing can be achieved with a 3D design of the plurality of channels in the displaceable structure. High pressure can be applied by using a piston to speed up the operation of the fluidic device. To perform fluorescence, absorbance, impedance analysis, the reservoirs can be replaced with light guides, fibers or other optical devices to optically connect light sources, filters and detectors to the fluidic sample.

FIGS. 12A-12E show a fluidic process that can be equivalent to the exemplary fluidic procedure for obtaining DNA as show in FIGS. 2A-2D and FIGS. 9A-9D. By way of example and not of limitation, FIG. 12B shows when a fluid such as a lysate is flowed from a first reservoir 1007 to a second reservoir 1008 through the channel arrangement 1005 containing the functional element 1006 (e.g., DNA binding matrix), the DNA is captured in the functional element 1006. Then, FIG. 12E shows the structure 1003 rotated such that the channel arrangement 1005 is now aligned with reservoirs 1009, 1010 and the fluid can be flowed from a third reservoir 1009 to a fourth reservoir 1010. Such process can be repeated according to the number of steps desired to perform the fluidic operation (e.g. DNA binding).

In some embodiments, a fluidic pressuring mechanism 1011 can be associated with the reservoirs 1007-1010 to facilitate movement of the fluid. By way of example and not of limitation, the fluidic pressuring mechanism 1011 can be pistons, actuators, pumps, or valves. Pistons can have various sizes and shapes, for example, to function with a syringe. Actuators can be internal to the reservoir or external to the reservoir. Pumps can also be internal or external to the reservoir, and can be electrochemical pumps, parasitic pumps, electro-osmotic pumps or vacuum pumps. In some embodiments, a membrane can be used to press down in the reservoir, thus forcing the fluid to flow. The fluidic pressure obtained from such fluidic pressuring mechanism can comprise positive or negative pressure. For example, the fluid can be pushed from the source of the fluid, or pulled from the destination of the fluid. However, those skilled in the art would understand that other types of pressuring mechanisms are possible to facilitate the movement of the fluid.

In some embodiments, the first reservoir 1007 can comprise elute buffer, while the second reservoir 1008 can comprise water. DNA can be eluted into the water and mixing can be performed by pushing the fluidic sample through the functional element 1006 (e.g., membrane) in the channel arrangement 1005. A reservoir of the final stage can be, for example, a microwell or a cartridge comprising a dry reagent, and the DNA can be deposited. In some embodiments, the reservoir can comprise a PCR buffer such that the PCR ready solution can be available without any dry reagents in a reaction structure. In some embodiments, the plurality of reservoirs can comprise wash buffers to wash the functional element, channels, or structure a desired number of times.

In some embodiments, a reservoir can comprise a lysate. The fluidic device can be configured such that the lysate flows through the functional element of the channel to lyse the desired cells. By way of example, the functional element can be an orifice for lysing particular cells, which is known by those skilled in the art. Alternatively, an electrical field can be applied to the channel. Another functional element can comprise a bead beating element to lyse desired cells. Consequently, a plurality of lysis operation can be performed and DNA can be extract using a single fluidic device having various functional elements.

Figure 13:
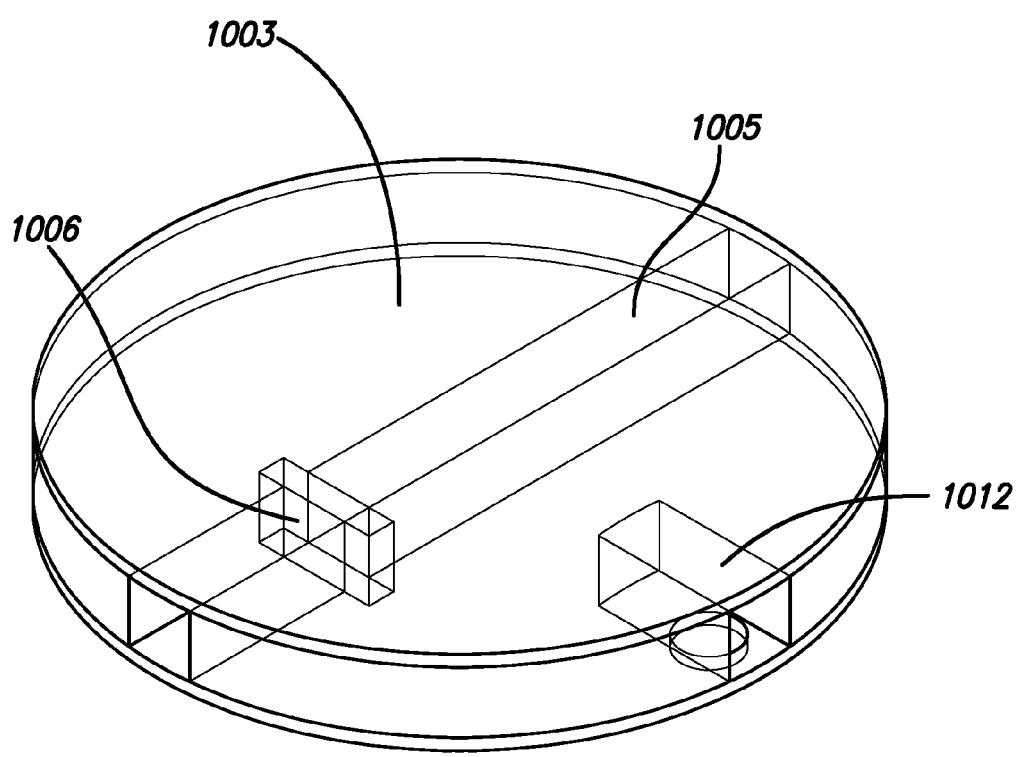
FIG. 13 shows the displaceable structure with a fluidic channel and a functional element.
Figure 14:
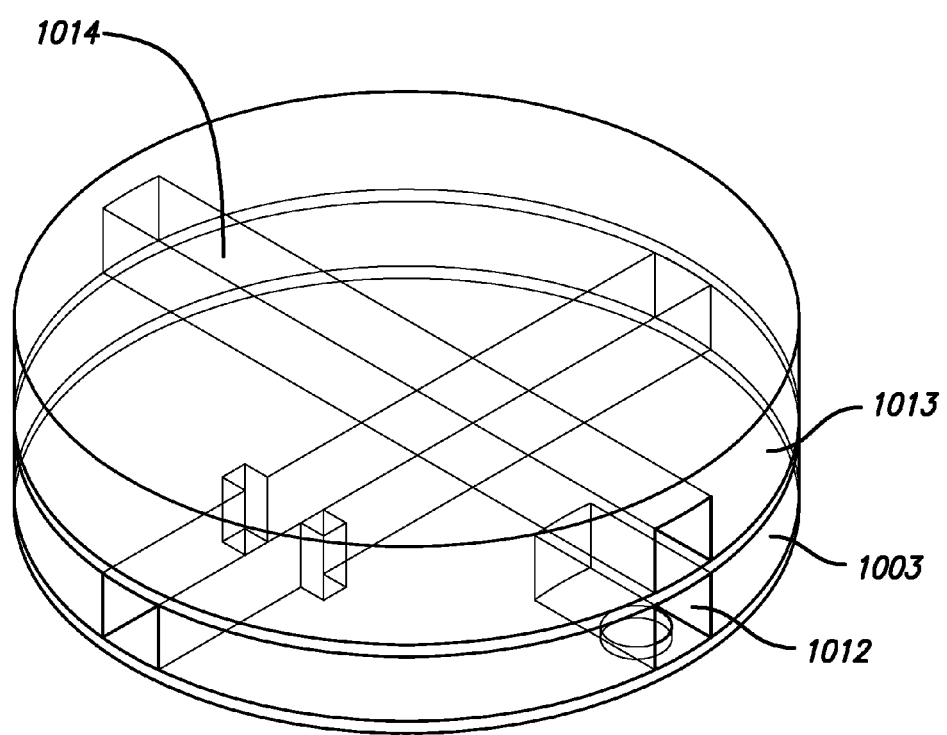
FIG. 14 shows a second displaceable structure located above another displaceable structure.

FIG. 13 shows a close up view of the displaceable structure 1003 having a channel arrangement 1005 with a functional element 1006. The exemplary displaceable structure 1003 is shown as a substantially disk shaped planar shape. However, the displaceable structure can have other shapes and sizes, for example, substantially spherical. Additionally, the structure 1003 can have a via 1012, as also shown in FIG. 14 with a second structure 1013 layered on the first structure 1003 and adapted to operate dependently or independently with the first structure 1003. In some embodiments, when two structures 1003, 1013 are layered upon one another, the structures can be aligned such that the via 1012 of the first structure 1003 can be aligned with the channel arrangement 1014 of the second structure 1013. Therefore, a reservoir can be connected with the via 1012 of the first structure 1003 and the fluid can flow through the channel arrangement 1014 of the second structure 1013, while maintaining minimal dead volume space. Vias facilitate the fluid to flow from one structure to another structure. Alternatively, tubing or integrated pathways can be utilized (similar to wires or jumpers in a PCB) to fluidly connect two or more channels.

Figure 15:
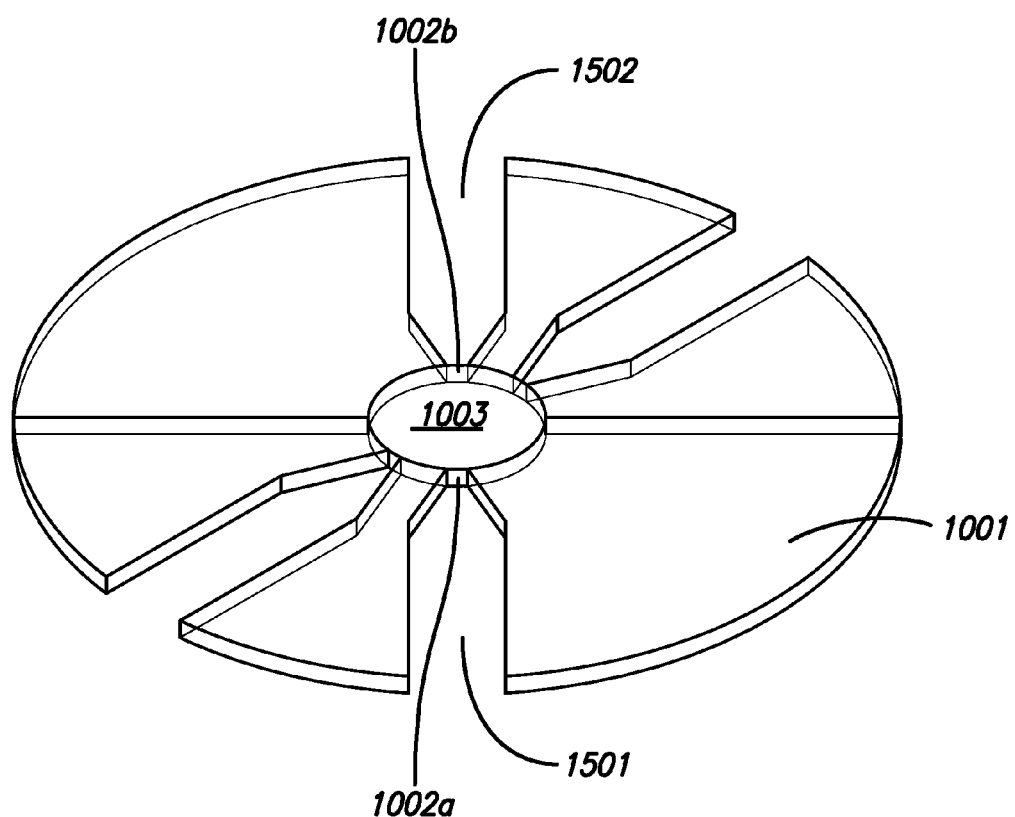
FIG. 15 shows a perspective view of the displaceable structure associated with an adapter.

FIG. 15 shows a perspective view of an exemplary adapter 1001 with the displaceable structure 1003 associated with the adapter 1001. The locations of the ports 1002a, 1002b can be shown on the structure 1003, with slots 1501, 1502 in the adapter 1001 such that reservoirs (e.g., syringes) can be connected with the structure 1003 through the ports 1002a, 1002b.

Figure 16:
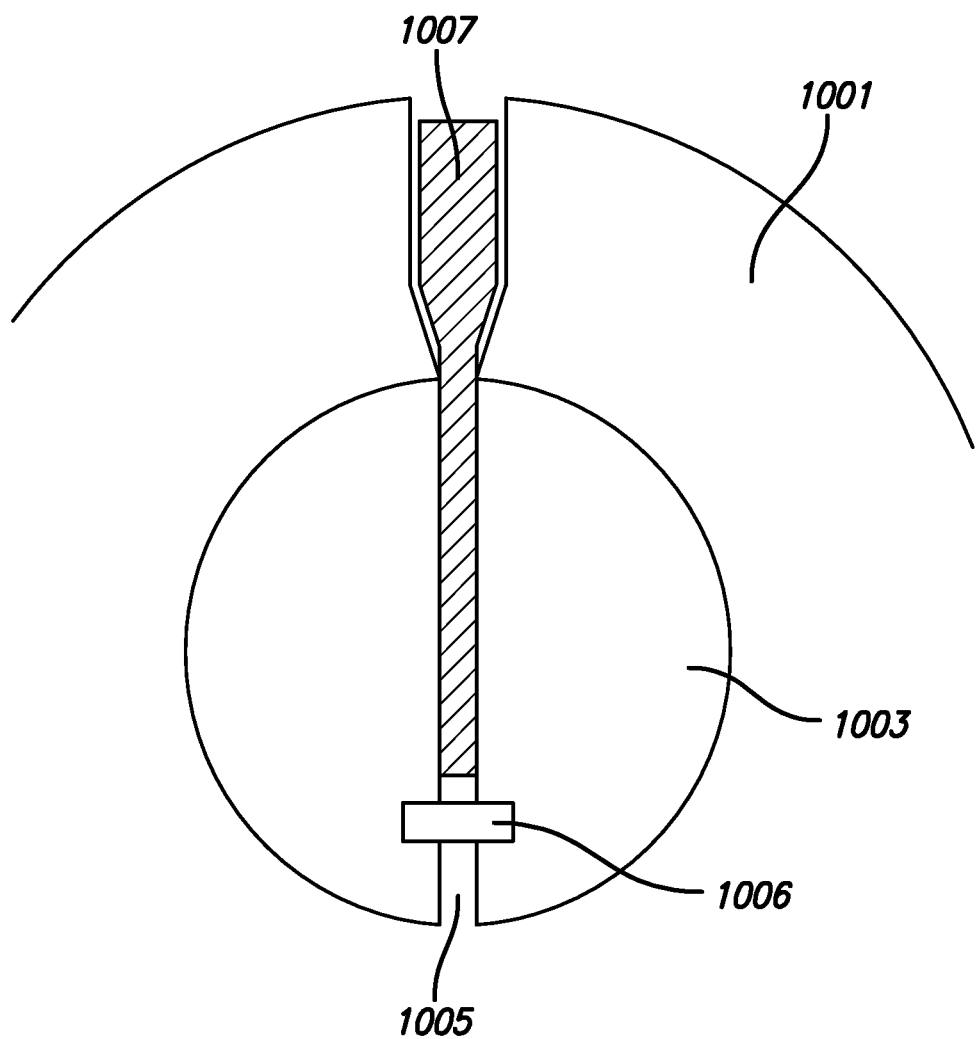
FIG. 16 shows a close-up cross-sectional view of the displaceable structure associated with the adapter.

FIG. 16 shows a close-up view of the displaceable structure 1003 with the adapter 1001 and an exemplary reservoir 1007 such as a syringe connected with the structure 1003. In some embodiments, the channel arrangement 1005 can be wide enough such that the fluid pressuring mechanism (e.g., a piston) can be configured to enter the channel arrangement 1005, thus requiring less pressure to move the fluid. The problem with the fluid material sticking to channel walls can be minimized since the piston can remove any material that may be stuck on the channel walls. Conveniently, wider channels can be easier to fabricate. A functional element 1006 is also shown in the fluidic path of the channel arrangement 1005.

Figure 17:
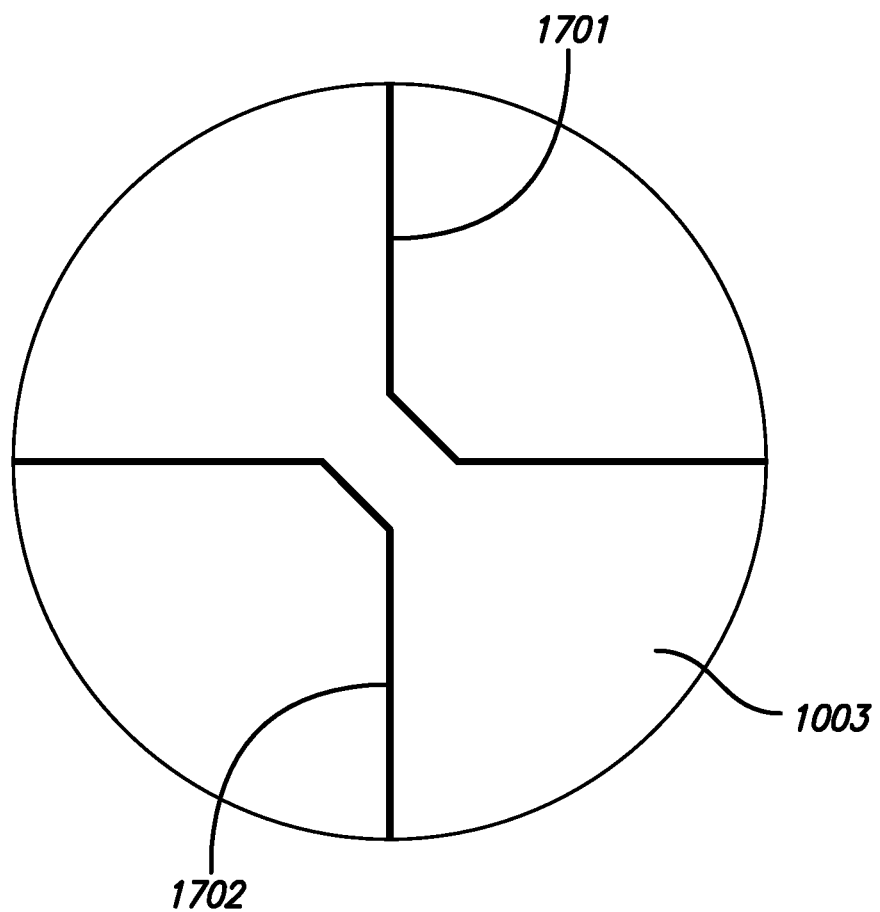
FIG. 17 shows a cross-sectional view of a possible configuration of two fluidic channels in the displaceable structure.
Figure 18C:
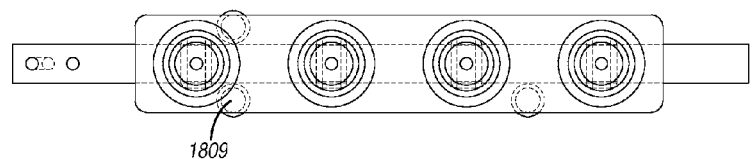
FIGS. 18A-18D show cross-sectional and perspective views of fluidic devices with a structure being slidably moveable in an axial direction.
Figure 18D:
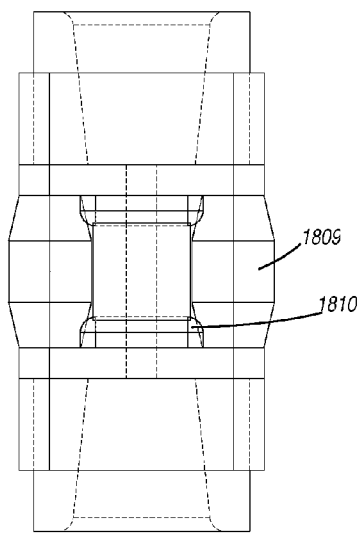
Figure 18A:
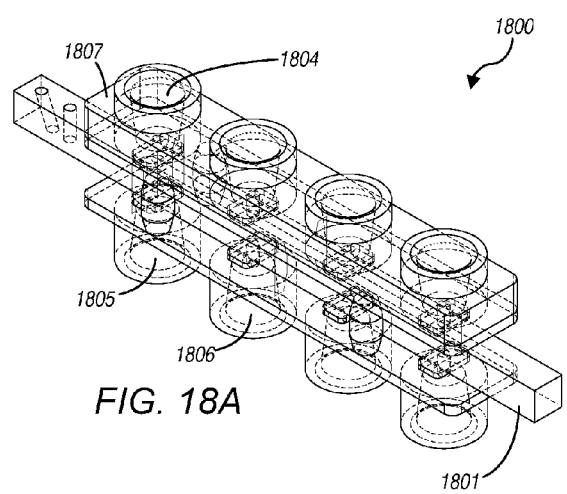
Figure 18B:
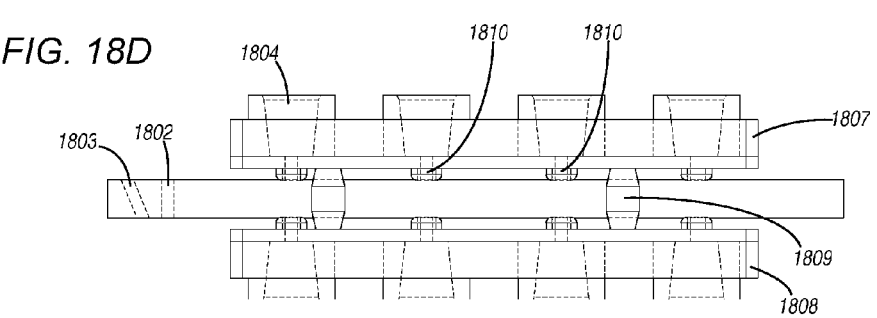

FIG. 17 shows a schematic drawing of an alternative channel arrangement in the displaceable structure 1003 where there are two separate channel arrangements 1701, 1702 for two distinct fluidic flow paths.

FIGS. 18A-18D show an alternative device 1800 for performing fluidic operations. In some embodiments, the slidably moveable structure 1801 can be a square or a substantially rectangular rod between two fixed structures 1807, 1808. The fixed structures 1807, 1808 can have ports for flowing fluids from one port 1804 on one of the fixed structures 1807 to a second port 1805 on the other fixed structure 1808, through the slidable moveable structure 1801. The slidable moveable structure 1801 can have more than one distinct fluidic paths. For example, a first fluidic path can be a substantially vertical fluidic path 1802, and a second fluidic path can be a substantially inclined fluidic path 1803. The slanted fluidic path can be used to flow fluid from the first port 1804 on one of the fixed structures 1807 to a second port 1806 on the other fixed structure 1808, thus fluidly connecting the two ports, wherein the two ports 1804, 1806 are not located directly across from one another.

In some embodiments, the ports can be a luer connection to connect the ports with, by way of example and not of limitation, syringes. In some embodiments, the ports can be a vertical hole to connect the ports with, by way of example and not of limitation, plungers. In some embodiments, the fixed structures 1807, 1808 can have guiding structures 1809 to facilitate guiding and sliding of the slidable moveable structure 1801 in alignment with the ports. The slidable moveable structure 1801 can be made of materials such as TEFLON®, plastic with a low friction coating, or other hydrophobic coating material. Hydrophobic coating material can minimize the changes of the fluid leaking out of the fluidic device 1800.

In some embodiments, the fixed structures 1807, 1808 can have sliding regions 1810 in which the slidable moveable rod 1801 can be configured to slide against. Therefore, the slidable moveable rod 1801 makes minimal contact with the fixed structures, thus minimizing the surface area and friction between the slidable moveable rod 1801 and the fixed structures.

In some embodiments, the slidable moveable rod 1801 can be larger than the vertical distance between the sliding regions thereby allowing the slidable moveable rod 1801 be compressed and fit snugly to create a seal. The slidable moveable rod 1801 can be adapted to expand in a horizontal direction to accommodate such compression in the vertical direction. Therefore, the guiding structures 1809 can be located on the fixed structures with consideration for expansion of the slidable moveable rod 1801.

Various devices according to the embodiments of the present disclosure can be used to perform plasma base pathogen detection (e.g., hepatitis). For example, a syringe containing blood can be connected with the luer connection port. A filter can be placed in the hole 1803, 1802 of the slidable moveable rod 1803 to capture cells yet allow plasma to pass through the filter. The lysate (e.g., blood) can be forced from the syringe, through the filter to a reservoir or another syringe on the other side of the filter. Next, a DNA binding matrix can be placed in the hole of the slidable moveable rod 1803 and the lysate can be forced from one reservoir to another, through the DNA binding matrix. By way of example and not of limitation, the separated cells can be used independently for various applications such as detecting malaria or HIV. A capillary effect can also be used for sample collection such as for finger pricks.

In some embodiments, can be desirable to have air in the fluidic devices described in various embodiments of the present disclosure. The air can be used to dry the channels and/or the functional elements, or push out any remaining fluid in the channels.

In some embodiments, dielectrophoresis can be performed in addition to filtering a sample concentration by way of evaporation. For example, a channel can be expanded and heated to control the flow of fluid from the channels. The shape of the channel can also be optimized to form a film of fluid in the channel to accelerate evaporation.

In some embodiments, the functional element can be a filteration element configured to allow dead cell components to pass through the filter. Accordingly, cells larger than a selected side based on the filter will be captured by the filter and smaller cell will pass through the filter.

In some embodiments, DNA extraction quality analysis can be performed by way of absorbance measurements. Thus, quality of the DNA can be determined before performing PCR reaction.

In some embodiments, a sample can be homogenized in the reservoir. By way of example and not of limitation, a rotational grinder can be installed in a syringe to homogenize the sample. Then the fluidic sample can be withdrawn or pulled by other reservoir (e.g., syringe) by pulling the plunger of the other syringe, thus creating a vacuum. Alternatively, the reservoir comprising the grinder can also be configured to push out the fluidic sample. Homogenization can be performed on samples such as food, tissue, feces and/or soil.

In some embodiments, various samples can be mixed in the reservoirs. For example, a first reservoir can comprise a first sample. Then, the first sample can be pushed to the second reservoir comprising a second sample. The second reservoir can comprise a 3D spiral shape to achieve thorough mixing. In some embodiments, if the texture of the reservoir does not facilitate ease of pushing out the sample, the sample can be pulled out by creating a vacuum as described previously.

In some embodiments, comprehensive tests can be performed using the fluidic device according to the present disclosure. Such test can measure protein concentration, bio markers, nucleic acids (both pathogenic and genomic) and analytes using analysis methods known by those skilled in the art. Cytometry can be performed to conduct cell based analysis. By way of example and not of limitation, after cell filtration, flow cytometry can be performed on one portion of the sample while the other undergoes sample preparation for ELISA, PCR, real-time PCR and/or qPCR. In some embodiments separate ELISA or ELISA with PCR tests can be performed by using the fluidic device according to the present disclosure, thus reducing health related problems.

In some embodiments, the fluidic device of the present disclosure can be used to separate blood serum, plasma and cells. Different filters can be implemented as the functional element in the moveable structure to achieve desired separation and analysis. In some embodiments, the functional element can be a bubble removal element (e.g., de-bubbler). In some embodiments, impedance spectroscopy can be performed.

In some embodiments, droplet generation of the fluid (e.g., sample) can be performed by precisely moving the moveable structure. By way of example and not of limitation, two reservoirs can perform droplets of oil emulsion, which can then be used for digital PCR. An array can be integrated into the system instead of cartridges to hold the droplets. A low cost system can be made using the device described in U.S. Patent Publication No. 20100321696 published on Dec. 23, 2010 and U.S. Patent Publication No. 20110207137 published on Aug. 25, 2011, for qPCR for digital PCR applications, both of which are incorporated by reference in their entirety. Such system can be robust, low cost and portable.

Examples of samples that can be processed using the fluidic device according to the present disclosure can include, but not be limited to swabs, whole blood, food parts (homogenized), stool, urine, other bodily fluids, soil, and/or forensic evidence.

In some embodiments, the fluidic device according to the present disclosure can be fabricated using plain plastic, polymer, and/or metal sheets and drawing holes in such material by drilling, laser cutting, using a water jet, EDM, etching and among other methods known by those skilled in the art. Injection molding methods can also be used. Other fabrication methods such as laser fabrication, xerography, and other semiconductor manufacturing processes. Low friction coatings and lubrication can be used to reduce friction of the moveable structure.

The examples set forth above are provided to give those of ordinary skill in the art a complete disclosure and description of how to make and use the embodiments of the present disclosure, and are not intended to limit the scope of what the inventors regard as their disclosure. Modifications of the above-described modes for carrying out the disclosure may be used by persons of skill in the art, and are intended to be within the scope of the following claims. All patents and publications mentioned in the specification may be indicative of the levels of skill of those skilled in the art to which the disclosure pertains. All references cited in this disclosure are incorporated by reference to the same extent as if each reference had been incorporated by reference in its entirety individually.

It is to be understood that the disclosure is not limited to particular methods or systems, which can, of course, vary. It is also to be understood that the terminology used herein is for the purpose of describing particular embodiments only, and is not intended to be limiting. As used in this specification and the appended claims, the singular forms "a", "an", and "the" include plural referents unless the content clearly dictates otherwise. The term "plurality" includes two or more referents unless the content clearly dictates otherwise. Unless defined otherwise, all technical and scientific terms used herein have the same meaning as commonly understood by one of ordinary skill in the art to which the disclosure pertains.

A number of embodiments of the disclosure have been described. Nevertheless, it will be understood that various modifications may be made without departing from the spirit and scope of the present disclosure. Accordingly, other embodiments are within the scope of the following claims.

The invention claimed is:

1. A device for performing fluidic operations, the device comprising:
 a fluidic chamber having a plurality of pairs of ports, a first port of each pair being located on a first side of the fluidic chamber and a second port of each pair being located on a second side of the fluidic chamber, each second port being opposite a respective first port;
 a plurality of reservoirs adapted to be fluidly connected with the fluidic chamber at each of the plurality of pairs of ports, the plurality of reservoirs configured to flow fluid from a first reservoir on the first side of the fluidic chamber through each of the first port and at least one of the second ports of the plurality of pairs of ports to a second reservoir on the second side of the fluidic chamber, or vice versa, wherein each reservoir of the plurality of reservoirs comprises a fluidic pressuring mechanism adapted to facilitate a movement of the fluid between the first reservoir and the second reservoir through the fluidic chamber, and vice versa; and a structure slidably moveable within the fluidic chamber, the slidably moveable structure comprising:
one or more openings through the structure and adapted to be aligned by a sliding of the structure within the fluidic chamber with at least one pair of the plurality of pairs of ports to allow fluidic connection between one or more reservoirs on the first side and respective one or more reservoirs on the second side, the one or more openings being moveably alignable with a desired pair of ports by the sliding of the structure to allow the movement of the fluid between the first reservoir, via the one or more openings therein through the slidably moveable structure, and the second reservoir, and vice versa; and
at least one interaction element disposed within at least one of the openings and operable for interacting with the fluid therein, the at least one interaction element comprising a functional element, which is located in a flow path of the fluid through the at least one of the openings when the fluid flows through the fluidic chamber, the functional element comprising one or more of a DNA binding matrix or a lysis structure.

2. The device according to claim 1, wherein the functional element, which is located in a flow path of the fluid through the at least one of the openings when the fluid flows through the fluidic chamber, further comprises a filtering component.

3. The device according to claim 2, wherein movement of the functional element through sliding of the slidably moveable structure is synchronous with movement of the opening comprising the functional element.

4. The device according to claim 1, wherein the structure is slidably moveable in an axial direction of the device.

5. The device according to claim 1, wherein the structure is slidably moveable in a radial direction of the device.

6. The device according to claim 1, wherein the fluidic pressuring mechanism is adapted to facilitate the movement of the fluid by one or more of a positive pressure or a negative pressure.

7. The device according to claim 1, wherein the pressuring mechanism is selected from the group consisting of: a piston, an internal actuator, an external actuator, and a pump.

8. The device according to claim 1, wherein the reservoirs are selected from the group consisting of: syringes, syringes with pistons, tubes with a pinching mechanism, pouches, planar reservoirs and channels, reservoirs with flexible membranes, pipettes, and cartridges.

9. The device according to claim 2, wherein the filtering component is selected from the group consisting of: a plasma filter, a cell filter, a mixing filter, and a binding filter.

10. A device for performing fluidic operations, the device comprising:
a first fixed structure and a second fixed structure, each having a plurality of ports;
a plurality of reservoirs adapted to be fluidly connected with the plurality of ports, the plurality of reservoirs configured to flow fluid from a first reservoir associated with the port on the first fixed structure, and connected to the port on the first fixed structure on a first side thereof, to a second reservoir associated with the port on the second fixed structure, and connected to the port on the second fixed structure on a side thereof opposite from the first reservoir, wherein each reservoir of the plurality of reservoirs comprises a fluidic pressuring mechanism adapted to facilitate a movement of the fluid between the first reservoir and the second reservoir, or vice versa, the pressuring mechanism comprising one or more of a piston, an internal actuator, an external actuator or a pump; and a structure slidably moveable between the first fixed structure and the second fixed structure, the slidably moveable structure comprising:
one or more openings through the structure and adapted to be aligned by a sliding of the structure with at least one port of the first fixed structure and at least one port of the second fixed structure to allow fluidic connection between one or more reservoirs associated with the first fixed structure, via the one or more openings therein through the slidably moveable structure, and respective one or more reservoirs associated with the second fixed structure, and vice versa; and
at least one interaction element disposed within at least one of the one or more openings and operable for interacting with the fluid therein.

11. The device according to claim 10, wherein the one or more openings of the structure are substantially vertically or inclinedly located within the structure.

12. The device according to claim 10, further comprising a plurality of sliding regions connected to the first fixed structure between the first fixed structure and the plurality of ports on the first fixed structure, and connected to the second fixed structure between the second fixed structure and the plurality of ports on the second fixed structure.

13. The device according to claim 10, wherein the plurality of ports comprises a Luer connection.

14. A method of performing fluidic operations using the device, which is described according to claim 1, the method comprising:
a) slidably moving the structure to align the at least one opening with a first pair of ports;
b) transferring the fluid from the reservoir on the first side of the fluidic chamber to the reservoir on the second side of the fluidic chamber by flowing the fluid through the functional element in the opening; and
c) repeating a)-b) a desired number of times.

15. The method according to claim 14, wherein the fluidic operation is extracting DNA.

16. The method according to claim 14, wherein the fluidic operation is lysating.

17. The method according to claim 14, wherein the fluidic operation is elution.

18. A device for performing fluidic operations, the device comprising:
a fluidic chamber having a plurality of pairs of ports, a first port of each pair being located on a first side of the fluidic chamber and a second port of each pair being located on a second side of the fluidic chamber, each second port being opposite a respective first port;
a plurality of reservoirs adapted to be fluidly connected with the fluidic chamber at each of the plurality of pairs of ports, the plurality of reservoirs configured to flow fluid from a first reservoir on the first side of the fluidic chamber through each of the first port and at least one of the second ports of the plurality of pairs of ports to a second reservoir on the second side of the fluidic chamber, or vice versa, wherein each reservoir of the plurality of reservoirs comprises a fluidic pressuring mechanism adapted to facilitate a movement of the fluid between the first reservoir and the second reservoir through the fluidic chamber, and vice versa, the pressuring mechanism comprising one or more of a piston, an internal actuator, an external actuator or a pump; and a structure slidably moveable within the fluidic chamber, the slidably moveable structure comprising:

one or more openings through the structure and adapted to be aligned by a sliding of the structure within the fluidic chamber with at least one pair of the plurality of pairs of ports to allow fluidic connection between one or more reservoirs on the first side and respective one or more reservoirs on the second side, the one or more openings being moveably alignable with a desired pair of ports by the sliding of the structure to allow the movement of the fluid between the first reservoir, via the one or more openings therein through the slidably moveable structure, and the second reservoir, and vice versa; and at least one interaction element disposed within at least one of the openings and operable for interacting with the fluid therein.

19. A device for performing fluidic operations, the device comprising:

a first fixed structure and a second fixed structure, each having a plurality of ports;

a plurality of reservoirs adapted to be fluidly connected with the plurality of ports, the plurality of reservoirs configured to flow fluid from a first reservoir associated with the port on the first fixed structure, and connected to the port on the first fixed structure on a first side thereof, to a second reservoir associated with the port on the second fixed structure, and connected to the port on the second fixed structure on a side thereof opposite from the first reservoir, wherein each reservoir of the plurality of reservoirs comprises a fluidic pressuring mechanism adapted to facilitate a movement of the fluid between the first reservoir and the second reservoir, or vice versa; and a structure slidably moveable between the first fixed structure and the second fixed structure, the slidably moveable structure comprising:

one or more openings through the structure and adapted to be aligned by a sliding of the structure with at least one port of the first fixed structure and at least one port of the second fixed structure to allow fluidic connection between one or more reservoirs associated with the first fixed structure, via the one or more openings therein through the slidably moveable structure, and respective one or more reservoirs associated with the second fixed structure, and vice versa; and at least one interaction element disposed within at least one of the one or more openings and operable for interacting with the fluid therein, the at least one interaction element comprising a functional element, which is located in a flow path of the fluid through the at least one of the openings when the fluid flows through the fluidic chamber, the functional element comprising one or more of a DNA binding matrix or a lysis structure.

\* \* \* \* \*